(12) United States Patent
Eaton et al.

(10) Patent No.: US 7,910,618 B2
(45) Date of Patent: Mar. 22, 2011

(54) ALBUMIN-BINDING CONJUGATES COMPRISING A FATTY ACID AND PEG

(75) Inventors: Michael Anthony Eaton, Watlington (GB); Timothy John Norman, Great Missenden (GB); John Robert Porter, Chinnor (GB)

(73) Assignee: UCB Pharma S.A., Brussels (BE)

( * ) Notice: Subject to any disclaimer, the term of this patent is extended or adjusted under 35 U.S.C. 154(b) by 832 days.

(21) Appl. No.: 11/597,962

(22) PCT Filed: May 25, 2005

(86) PCT No.: PCT/GB2005/002084
§ 371 (c)(1),
(2), (4) Date: Jul. 10, 2007

(87) PCT Pub. No.: WO2005/117984
PCT Pub. Date: Dec. 15, 2005

(65) Prior Publication Data
US 2008/0096957 A1    Apr. 24, 2008

(30) Foreign Application Priority Data
Jun. 1, 2004   (GB) .................................. 0412181.0

(51) Int. Cl.
*A01N 43/36* (2006.01)
(52) U.S. Cl. ...................................... 514/425; 548/546
(58) Field of Classification Search .................. 514/425; 548/546
See application file for complete search history.

(56) References Cited

FOREIGN PATENT DOCUMENTS

| WO | WO00/26256 | | 5/2000 |
|---|---|---|---|
| WO | WO 02/065985 | * | 8/2002 |
| WO | WO02/065985 | | 8/2002 |
| WO | WO03/022210 | | 3/2003 |
| WO | WO 03/022210 | * | 3/2003 |
| WO | WO 03/049684 | * | 6/2003 |
| WO | WO03/049684 | | 6/2003 |

OTHER PUBLICATIONS

Allen T Met Al: Biochimica Et Biophysica Acta, Amsterdam, NL, vol. 1237, No. 2, Jul. 26, 1995, pp. 99-108.*
Knudsen Lotte B et al: Journal of Medicinal Chemistry, American Chemical Society. Washington, US, vol. 43, No. 9, May 4, 2000, pp. 1 664-1669.*
Hamilton-Wessler Met Al.: Diabetologia, vol. 42, 1999, pp. 1254-1263.*
Kurtzhals, Peter et al., "Albumin Binding of Insulins Acylated with Fatty Acids: Characterization of the Ligand-Protein Interaction and Correlation Between Binding Affinity and Timing of the Insulin Effect in vivo", Biochem. J., 1995, vol. 312, pp. 725-731.
Allen, Theresa M. et al., "A New Strategy for Attachment of Antibodies to Sterically Stabilized Liposomes Resulting in Efficient Targeting to Cancer Cells", Biochimica et Biophysica Acta, 1995, vol. 1237, pp. 99-108.
Knudsen, Lotte B. et al., "Potent Derivatives of Glucagon-Like Peptide-1 with Pharmacokinetic Properties Suitable for Once Daily Administration", J. Med. Chem., 2000, vol. 43, pp. 1664-1669.
Hamilton-Wessler, M. et al., "Mechanism of Protracted Metabolic Effects of Fatty Acid Acylated Insulin, NN304, in Dogs: Retention of NN304 by Albumin", Diabetologia, 1999, vol. 42, pp. 1254-1263.
International Search Report for PCT/GB2005/002084 dated May 9, 2006.

* cited by examiner

*Primary Examiner* — Deborah D Carr
(74) *Attorney, Agent, or Firm* — McDonnell Boehnen Hulbert & Berghoff LLP

(57) ABSTRACT

The present invention provides an albumin-binding compound essentially of the following elements: a spacer group, a water-soluble bridging group, a fatty acid chain and an acidic group characterised in that the acidic group is attached to the distal end of the fatty acid chain. The invention also provides an albumin-binding compound to which one or more biologically active moieties are attached.

15 Claims, No Drawings

ALBUMIN-BINDING CONJUGATES COMPRISING A FATTY ACID AND PEG

The present invention relates to compounds capable of binding albumin for use in extending the in vivo serum half-life of proteins or peptides to which they are attached. More specifically the invention relates to molecules comprising one or more biologically active moieties to which one or more fatty acid chains capable of binding albumin are attached. Methods for the production of such molecules, and pharmaceutical compositions containing them, are also provided.

The use of fatty acids which bind albumin to increase in vivo half life of insulin was described by Kurtzhals et al., 1995, *Biochem. J.*, 312, 725-731. Insulin derivatives with affinity for albumin were produced by acylation of insulin with fatty acids.

The attachment of fatty acids to antibodies has been described in WO00/26256 and WO03/049684.

The present invention provides new compounds which are capable of binding albumin for use in extending the half-life of biologically active moieties to which they are attached. Thus, the present invention provides albumin-binding compounds consisting essentially of the following elements: a spacer group, a water-soluble bridging group, a fatty acid chain and an acidic group. The compounds are characterised in that the acidic group is attached to the distal end of the fatty acid chain. Each of the elements are as defined herein below. In one example the present invention provides albumin-binding compounds consisting essentially of:

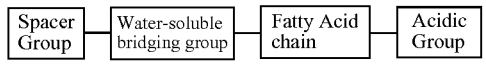

In another example the present invention provides albumin-binding compounds consisting essentially of:

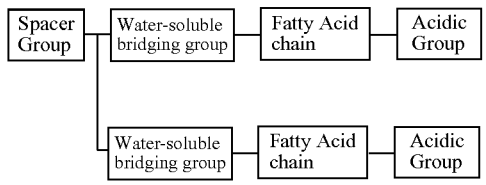

In a further example the present invention provides albumin-binding compounds consisting essentially of:

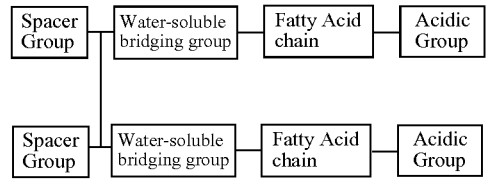

In a further example the present invention provides albumin-binding compounds consisting essentially of:

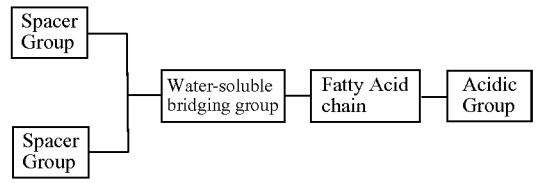

It will be appreciated by persons skilled in the art that each of the component elements may be linked together using suitable linker groups or bonds, including for example those described herein below.

Also provided by the present invention are albumin-binding compounds attached to one or more biologically active moieties. Therefore examples of the present invention include compounds consisting essentially of:

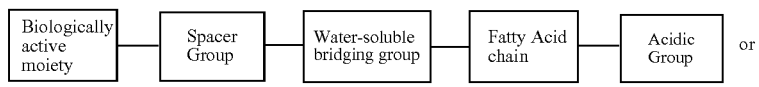
or

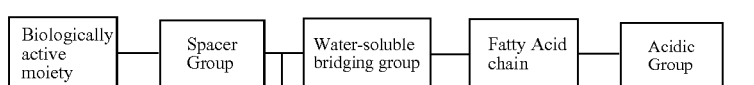
or

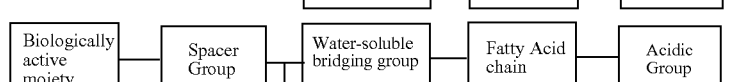

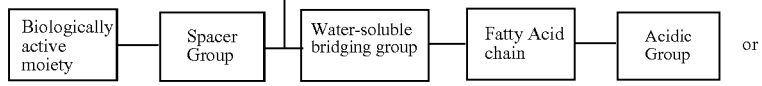
or

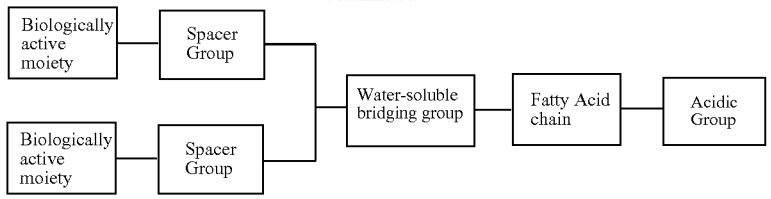

Particular examples of the present invention are provided in formula (I), (II), (II) or (IV):

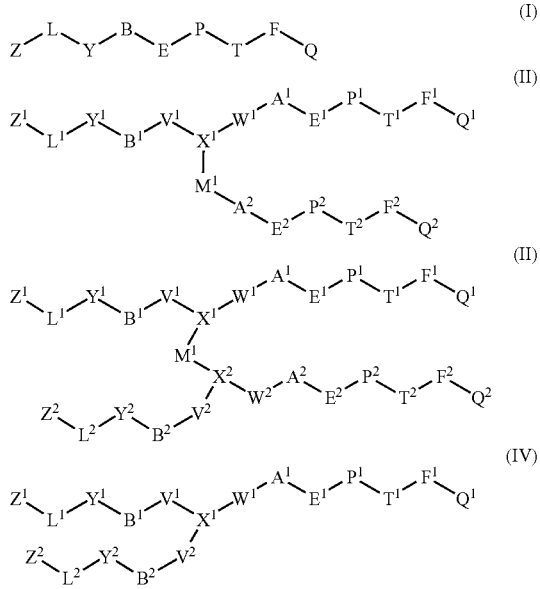

wherein:

Z, $Z^1$ and $Z^2$ independently represent the residue of a biologically active moiety;

L, $L^1$ and $L^2$ independently represent a spacer group;

Y, $Y^1$ and $Y^2$ independently represent a covalent bond, $-(CH_2)_y-$,

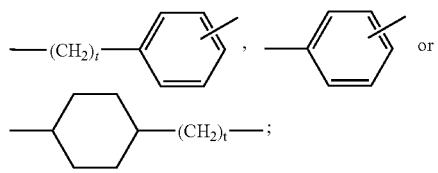

B, $B^1$ and $B^2$ are independently absent or represent $-CONH-$, $-NHCO-$, $-CO-$, $-OC(O)N(R^2)-$, $-N(R^2)C(O)O-$ or $-NHCONH-$;

$V^1$ and $V^2$ independently represent a covalent bond or $-(CH_2)_v-$;

$X^1$ and $X^2$ independently represent $CR^1$ or N;

$M^1$ represents a covalent bond or $-(CH_2)_m-$;

$W^1$ and $W^2$ independently represent a covalent bond or $-(CH_2)_w-$;

$A^1$ and $A^2$ independently represent $-CONH-$, $-NHCO-$, $-CO-$, $-OC(O)N(R^2)-$, $-N(R^2)C(O)O-$ or $-NHCONH-$;

E, $E^1$ and $E^2$ independently represent a covalent bond or $-(CH_2)_e-$;

P, $P^1$ and $P^2$ independently represent a water-soluble bridging group;

T, $T^1$ and $T^2$ independently represent a covalent bond or a linker group;

F, $F^1$ and $F^2$ independently represent a fatty acid chain;

Q, $Q^1$ and $Q^2$ independently represent an acidic group;

$R^1$ represents hydrogen or $C_{1-4}$ alkyl;

$R^2$ represents hydrogen or $C_{1-4}$ alkyl;

e is 1, 2, 3 or 4;

v is 1, 2, 3 or 4;

w is 1, 2, 3 or 4;

y is 1, 2, 3, 4, 5 or 6; and m is 1, 2 or 3.

As used herein, the term "$C_{1-4}$ alkyl" refers to straight-chained and branched alkyl groups containing 1 to 4 carbon atoms. Such groups are methyl, ethyl, n-propyl, isopropyl, n-butyl, isobutyl, sec-butyl and tert-butyl.

As used herein, the term "fatty acid chain" refers to the hydrocarbon backbone of fatty acids (excluding the terminal acidic group) containing 2 to 40 carbon atoms. Preferably the fatty acid chain for use in the present invention contains between 6 and 40 carbon atoms, more preferably between 10 and 30 carbon atoms, even more preferably between 15 and 25 carbon atoms. It will be appreciated that fatty acid chain length may be selected on the basis of the intended use of the product and required circulating half-life. Fatty acids for use in the present invention may be saturated or may contain one or more units of unsaturation. Suitable fatty acids for use in the present invention include, for example, n-dodecanoate ($C_{12}$, laurate), n-tetradecanoate ($C_{14}$, myristate), n-hexadecanoate ($C_{16}$, palmitate), n-octadecanoate ($C_{18}$, stearate), n-eicosanoate ($C_{20}$, arachidate), n-docosanoate ($C_{22}$, behenate), n-tetracosanoate ($C_{24}$), n-triacontanoate ($C_{30}$), n-tetracontanoate ($C_{40}$), cis-$\Delta^9$-octadecanoate ($C_{18}$, oleate) and all cis-$\Delta^{5,8,11,14}$-eicosatetraenoate ($C_{20}$, arachidonate).

Preferably the fatty acid chain for use in the present invention is a straight chain of between 14 and 24 carbon atoms. In one embodiment the fatty acid chain is a straight chain of 17 carbon atoms. In another embodiment the fatty acid chain is a straight chain of 23 carbon atoms.

As used herein, the term "residue" will be understood to mean that portion of a biologically active moiety which remains after it has undergone a substitution reaction as such terminology is familiar to the person skilled in the art.

As used herein the term 'water-soluble bridging group' refers to any substantially water-soluble moiety familiar to the person skilled in the art which is capable of forming a bridge between the spacer group and the fatty acid chain. In particular, the water-soluble bridging group, P, $P^1$ or $P^2$ will suitably comprise any substantially water-soluble moiety familiar to the person skilled in the art which is capable of forming a bridge between E, $E^1$ and $E^2$ and T, $T^1$ and $T^2$ respectively.

Examples of water-soluble bridging groups include water-soluble oligo- and poly-peptides comprising amino acids such as aspartic acid and/or glutamic acid; water-soluble mono-, di- and oligosaccharides such as glucose, glucosamine, lactose, sucrose or maltose; cyclodextrins; uronic acids; and branched or unbranched polysaccharides, e.g. a homo- or heteropolysaccharide such as amylose, dextran or glycogen.

Further examples of water-soluble bridging groups include any synthetic or naturally occurring substantially water-soluble, substantially non-antigenic polymer or copolymer, including, for example, optionally substituted straight or branched chain polyalkylene, polyalkenylene, or polyoxyalkylene polymers or the polymer N-(2-hydroxypropyl) methacrylamide (HPMA). Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol), poly(vinylalcohol) or derivatives thereof, especially optionally substituted poly(ethyleneglycol).

Preferably the water-soluble bridging group for use in the present invention is a polymer, preferably a polyalkylene oxide such as polyethylene glycol (PEG). As regards attaching PEG moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C.; and "Bioconjugation Protein Coupling Techniques for the Biomedical Sciences", 1998, M. Aslam and A. Dent, Grove Publishers, New York. Suitable molecular weight PEG molecules for use in the present invention range from 500 to 5,000. Particular PEG molecules include t-Boc-PEG-NHS, MW 3400; NHS-PEG-MAL, MW 3400; and NHS-PEG-MAL MW 2000 (obtainable from Nektar, formerly Shearwater).

The water-soluble bridging group, P, $P^1$ and $P^2$ in the compounds of formula (I), (II), (III) and (IV) above will suitably be a substantially water-soluble, substantially non-antigenic polymer. Typical polymers of which P, $P^1$ and $P^2$ are examples include polyalkylene oxides such as polyethylene glycols (PEGs).

Preferably P, $P^1$ and $P^2$ are polymer moieties comprising the repeating unit [$OCH_2CH_2$], where n is between 5 and 100. In one embodiment n is between 5 and 15, preferably either 5 or 12. In another embodiment n is between 40 and 100, preferably between 40 and 80. The repeating units may be separated by one or more connecting groups, examples of which include —$CH_2CONH$—, —$CONHCH_2$—, —$(CH_2)_2NHCO$—, —$NHCO$—, —$NHCOCH_2$—, —$CONH$— and —$(CH_2)_2NHCONH$—.

Suitably, $P^1$ and $P^2$ are identical.

The term 'biologically active moiety' as used herein refers to a biologically active compound having an available residue for attachment to the compounds of the present invention. Biologically active compounds for use in the present invention are compounds suitable for medicinal or diagnostic use in the treatment of animals, including humans.

Examples of biologically active moieties may include cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Biologically active moieties also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other biologically active moieties may include radionuclides such as $^{111}In$ and $^{90}Y$, $Lu^{177}$, $Bismuth^{213}$, $Californium^{252}$, $Iridium^{192}$ and $Tungsten^{188}/Rhenium^{188}$; or drugs such as but not limited to, alkylphosphocholines, topoisomerase I inhibitors, taxoids and suramin.

Other biologically active moieties include proteins, peptides and enzymes. Enzymes of interest include, but are not limited to, proteolytic enzymes, lyases, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Typical biologically active moieties of which $Z^1$, $Z^2$ and $Z^3$ are residues include antibodies and antibody fragments. Thus, the residues Z, $Z^1$ and $Z^2$ include residues of whole antibodies and functionally active fragments or derivatives thereof and may be, but are not limited to, polyclonal, monoclonal, multi-valent, multi-specific, humanized or chimeric antibodies, single chain antibodies, Fab fragments, Fab' and F(ab')$_2$ fragments and epitope-binding fragments of any of the above.

Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD or IgA) or subclass of immunoglobulin molecule.

Monoclonal antibodies may be prepared by any method known in the art such as the hybridoma technique (Kohler & Milstein, *Nature,* 1975, 256, 495-497), the trioma technique, the human B-cell hybridoma technique (Kozbor et al., *Immunology Today,* 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA,* 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., *Nature,* 1983, 305, 537-539; WO 93/08829; Traunecker et al., *EMBO J.* 1991, 10, 3655-3659). Multivalent antibodies may comprise multiple specificities or may be monospecific (see, for example, WO 92/22853).

The antibodies for use in the present invention can also be generated using various phage display methods known in the art and include those disclosed by Brinkman et al., *J. Immunol. Methods,* 1995, 182, 41-50; Ames et al., *J. Immunol. Methods,* 1995, 184, 177-186; Kettleborough et al. *Eur. J. Immunol.,* 1994, 24, 952-958; Persic et al., *Gene,* 1997 187, 9-18; and Burton et al., *Advances in Immunology,* 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108. Techniques for the production of single chain antibodies, such as those described in U.S. Pat. No. 4,946,778, can also be adapted to produce single chain antibodies. Also, transgenic mice, or other organisms, including other mammals, may be used to express humanized antibodies.

In one example the antibody fragments are Fab' fragments which possess a native or a modified hinge region. A number of modified hinge regions have already been described, for example, in U.S. Pat. No. 5,677,425, WO9915549, and WO9825971 and these are incorporated herein by reference.

Particular antibody fragments also include those described in WO2005003169, WO2005003170 and WO2005003171.

Where the biologically active moiety is an antibody, said antibody will in general be capable of selectively binding to an antigen. The antigen may be any cell-associated antigen, for example a cell surface antigen on cells such as bacterial cells, yeast cells, T-cells, endothelial cells or tumour cells, or it may be a soluble antigen. Antigens may also be any medically relevant antigen such as those antigens upregulated during disease or infection, for example receptors and/or their corresponding ligands. Particular examples of cell surface antigens include adhesion molecules, for example integrins such as P1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD45, CDW52, CD69, carcinoembryonic antigen (CEA), human milk fat globulin (HMFG1 and 2), MHC Class I and MHC Class II antigens, and VEGF, and where appropriate, receptors thereof. Soluble antigens include interleukins such as IL-1, IL-2, IL-3, IL-4, IL-5, IL-6, IL-8, IL-12, IL-16 or IL-17, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof.

Suitably, $Z^1$ and $Z^2$ are identical.

The spacer groups for use in the present invention, will suitably comprise any moiety familiar to the person skilled in the art which is capable of forming a bridge between the water-soluble bridging group and the biologically active moiety. In particular the spacer groups L, $L^1$ and $L^2$ will suitably comprise any moiety familiar to the person skilled in the art which is capable of forming a bridge between Y, $Y^1$ and $Y^2$ and the residue Z, $Z^1$ and $Z^2$ respectively. For example, where Z, $Z^1$ or $Z^2$ is the residue of an antibody or a fragment thereof containing a cysteine residue the corresponding spacer group L, $L^1$ or $L^2$ will suitably be a succinimide (i.e. the reaction product of a maleimide residue with the cysteine-containing polypeptide residue Z, $Z^1$ or $Z^2$ via a thiol linkage) linked to Y, $Y^1$ or $Y^2$ through its nitrogen atom.

Suitably, $L^1$ and $L^2$ are identical.

The presence of the distal acidic group enables the compounds of the present invention to bind albumin more effectively than compounds where the acidic group is absent altogether; or where the acidic group is incorporated into the framework of the molecule e.g. via an acyl(ester) or amide link, for instance where the fatty acid unit is facing the 'opposite' direction leaving the lipid (hydrocarbon) chain of the fatty acid exposed. Examples of suitable acidic groups for use in the present invention include carboxylic, phosphonic, phosphinic, sulphinic and sulphonic acid groups Q, $Q^1$ and $Q^2$ therefore represent an acidic group, preferably carboxyl, phosphonic, phosphinic, sulphinic or sulphonic acid groups.

In one embodiment, Q represents $CO_2H$.
In one embodiment, $Q^1$ represents $CO_2H$.
In one embodiment, $Q^2$ represents $CO_2H$.
Suitably $Q^1$ and $Q^2$ are identical.

The linker groups T, $T^1$ and $T^2$ will suitably comprise any moiety familiar to the person skilled in the art which is capable of forming a bridge between the fatty acid chain F, $F^1$ and $F^2$ and the water-soluble bridging group P, $P^1$ and $P^2$ respectively.

Typical examples of T, $T^1$ and $T^2$ include a covalent bond, —CONH—, —OCH$_2$CONH—, —OCONH— and —NHCO—.

In one embodiment, T represents —CONH—. In another embodiment, T represents —NHCO—. In another embodiment, T represents a covalent bond.

In another embodiment, T represents —OCH$_2$CONH—.

In one embodiment, $T^1$ represents —CONH—. In another embodiment, $T^1$ represents —NHCO—. In another embodiment, $T^1$ represents a covalent bond. In a preferred embodiment, $T^1$ represents —OCONH—.

In one embodiment, $T^2$ represents —CONH—. In another embodiment, $T^2$ represents —NHCO—. In another embodiment $T^2$ represents a covalent bond. In a preferred embodiment, $T^2$ represents —OCONH—.

Suitably $T^1$ and $T^2$ are identical.

In one embodiment, $X^1$ represents $CR^1$. In another embodiment, X represents N.

In one embodiment, $X^2$ represents $CR^1$. In another embodiment, X represents N.

Suitably $X^1$ and $X^2$ are identical.

Suitably $A^1$ represents —CONH—, —NHCO—, —CO—, —OC(O)N($R^2$)—, —N($R^2$)C(O)O— or —NHCONH—. In one embodiment, $A^1$ represents —CONH—. In another embodiment, $A^1$ represents —NHCO—.

Suitably $A^2$ represents —CONH—, —NHCO—, —CO—, —OC(O)N($R^2$)—, —N($R^2$)C(O)O— or —NHCONH—. In one embodiment, $A^2$ represents —CONH—. In another embodiment, $A^2$ represents —NHCO—.

Suitably $A^1$ and $A^2$ are identical.

Suitably B represents —CONH—, —NHCO—, —CO—, —OC(O)N($R^2$)—, —N($R^2$)C(O)O— or —NHCONH. In one embodiment, B represents —CONH—. In another embodiment, B represents —NHCO—.

Suitably $B^1$ represents —CONH—, —NHCO—, —CO—, —OC(O)N($R^2$), —N($R^2$)C(O)O— or —NHCONH. In one embodiment, $B^1$ represents —CONH—. In another embodiment, $B^1$ represents —NHCO—. Where $B^1$ represents —CONH—, $X^1$ typically represents CH.

Suitably $B^2$ represents —CONH—, —NHCO—, —CO—, —OC(O)N($R^2$)—, —N($R^2$)C(O)O— or —NHCONH. In one embodiment, $B^2$ represents —CONH—. In another embodiment, $B^2$ represents —NHCO—. Where $B^2$ represents —CONH—, $X^2$ typically represents CH.

Suitably $B^1$ and $B^2$ are identical.

In a preferred embodiment, $V^1$ represents a covalent bond. In another embodiment, $V^1$ represents —$(CH_2)_v$— in which v is as defined above.

In a preferred embodiment, $V^2$ represents a covalent bond. In another embodiment, $V^2$ represents —$(CH_2)_v$— in which v is as defined above.

Suitably, $V^1$ and $V^2$ are identical.

In one embodiment, $W^1$ represents a covalent bond. In another embodiment, $W^1$ represents —$(CH_2)_w$— in which w is as defined above.

In one embodiment, $W^2$ represents a covalent bond. In another embodiment, $W^2$ represents —$(CH_2)_w$— in which w is as defined above.

Suitably, $W^1$ and $W^2$ are identical.

Suitably, $Y^1$ and $Y^2$ are identical.

In one embodiment, $M^1$ represents a covalent bond. In another embodiment, $M^1$ represents —$(CH_2)_m$— in which m is as defined above.

In a preferred embodiment, $R^1$ is hydrogen. In another embodiment, $R^1$ represents $C_{1-4}$alkyl, especially methyl.

In a preferred embodiment, $R^2$ is hydrogen. In another embodiment, $R^2$ represents $C_{1-4}$alkyl, especially methyl.

In one embodiment y is 2. In another embodiment, y is 4.

In one embodiment m is 1. In another embodiment, m is 2. In an additional embodiment, m is 3. Favourably, m is 3.

In one embodiment e is 1. In another embodiment, e is 2. In another embodiment, e is 3.

In another aspect, the present invention provides novel compounds which are valuable intermediates for the attachment of biologically active moieties of which Z, $Z^1$ and $Z^2$ are residues. Thus, the invention also provides compounds of formula (V), (VI), (VII) and (VIII):

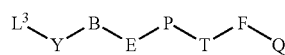
(V)

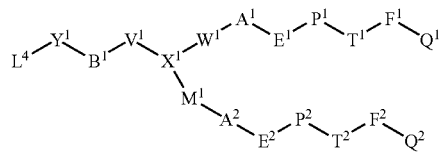
(VI)

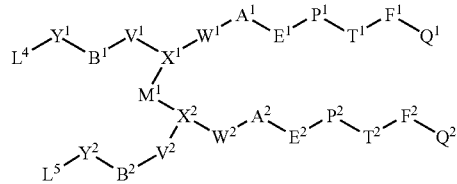
(VII)

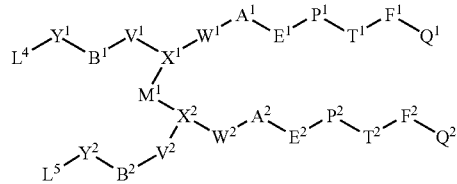

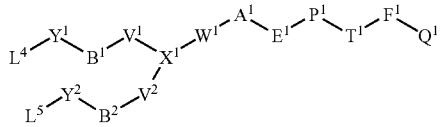
(VIII)

wherein
$L^3$, $L^4$ and $L^5$ represent groups capable of attaching the residue Z, $Z^1$ and $Z^2$ respectively, or capable of being converted into such groups; and each of the other variables is as defined above in relation to formula (I), (II), (III) or (IV).

Where Z, $Z^1$ or $Z^2$ is the residue of a polypeptide molecule (e.g. an antibody or a fragment thereof), the corresponding group $L^3$, $L^4$ or $L^5$ may be attached to the polypeptide through any available amino acid side-chain or terminal amino acid functional group located in the antibody fragment, for example any free amino, imino, thiol, hydroxy or carboxyl group. Such amino acids may occur naturally in, for example, the antibody fragment or may be engineered into the fragment using recombinant DNA methods (see, for example, U.S. Pat. No. 5,677,425 and U.S. Pat. No. 5,219,996). In a preferred aspect of the invention the two groups are covalently linked through a thiol group of a cysteine residue located in the antibody or fragment thereof, preferably in the hinge. The covalent linkage will generally be a disulphide bond or a sulphur-carbon bond, preferably the latter. In one example where a thiol group is used as the point of attachment appropriately activated groups, for example thiol-selective derivatives such as maleimide and cysteine derivatives, may be used.

In a preferred feature, the groups $L^3$, $L^4$ and $L^5$ are identical and represent maleimide derivatives attached to the remainder of the molecule through the maleimide nitrogen atom. In another feature, Q, $Q^1$ and $Q^2$ are identical and represent $CO_2H$. Accordingly, one illustrative subset of the compounds of formula (V), (VI), (VII) and (VIII) above is represented by the compounds of formula (IX), (X), (XI) and (XII):

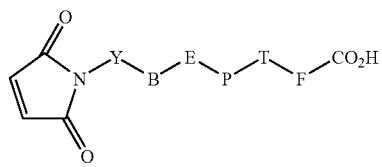
(IX)

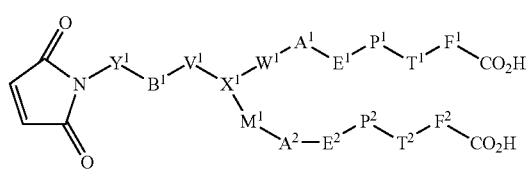
(X)

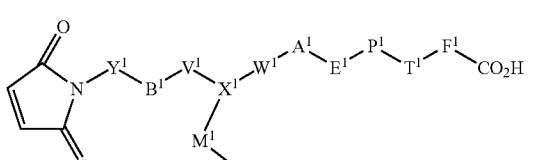
(XI)

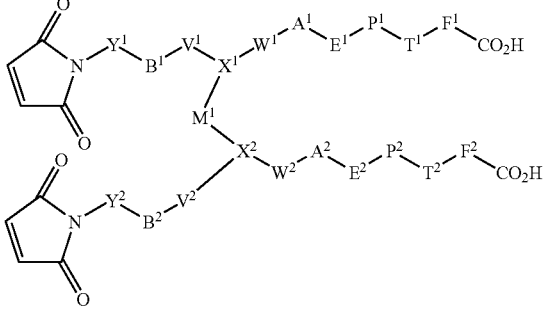

-continued

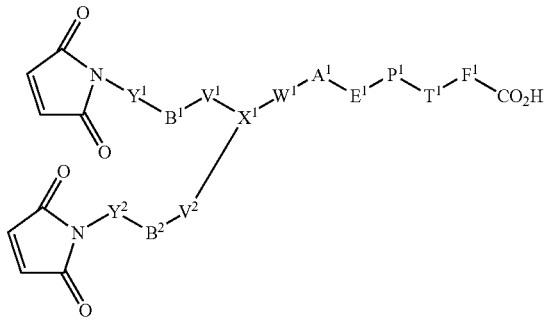

(XII)

Wherein Each of the Variables is as Defined Above.

According to a further aspect of the invention there is provided a pharmaceutical composition which comprises a compound of formula (I), (II), (III) or (IV) in association with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I), (II), (III) and (IV) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I), (II), (III) and (IV) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of the present invention may be prepared by using methods analogous to those in the Examples provided herein.

For example, the compounds of formula (I), (II), (III) and (IV) may be prepared by a process which comprises attachment of residue Z, $Z^1$ and $Z^2$ to a compound of formula (IX), (X), (XI) or (XII) respectively using procedures which are well known to the person skilled in the art.

The compounds of formula (V) wherein T is —CONH— may be prepared by a process which comprises reacting a compound of formula (XIII) with a compound of formula (XIV):

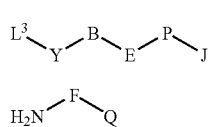

(XIII)

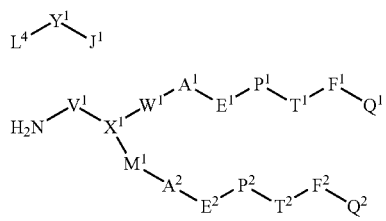

(XIV)

wherein J represents an activated carboxylate moiety; and the remaining variables are as defined above.

Examples of activated carboxylate moieties for the substituent J include acid chlorides; acid anhydrides; and the ester formed when a carboxylic acid (J=—CO$_2$H) is reacted with N-hydroxysuccinimide.

The reaction between compounds (XIII) and (XIV) is conveniently effected in a suitable solvent, e.g. N,N-dimethylformamide, typically in the presence of an organic base, e.g. triethylamine.

The compounds of formula (VI) wherein B$^1$ is —CONH— may be prepared by a process which comprises reacting a compound of formula (XV) with a compound of formula (XVI):

(XV)

(XVI)

wherein J$^1$ represents an activated carboxylate moiety as defined above for J; and the remaining variables are as defined above.

The reaction between compounds (XV) and (XVI) is conveniently effected in a suitable solvent, e.g. dichloromethane, typically in the presence of an organic base e.g. triethylamine.

Where they are not commercially available, the compounds of formula (XIII), (XIV), (XV) and (XVI) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as gel permeation chromatography; cation or anion exchange; preparative HPLC; or column chromatography utilising, for example, silica and/or alumina in conjunction with an appropriate solvent system.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following non-limiting Examples illustrate the invention.

Intermediate 1

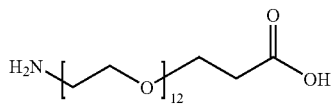

Fmoc-amino PEG12-propionic acid, MW 840 (150 mg) purchased from Polypure AS was dissolved in 1:4 piperidine: DMF (3 ml) and the solvent then removed after 10 min. The residue was dissolved in water (30 ml) and washed with Et$_2$O (4×30 ml) and DCM (4×30 ml). The aqueous layer was then acidified with 0.1M HCl and once again washed with DCM (3×30 ml). The water was removed, the residue dissolved in DCM, dried over MgSO$_4$ and the solvent removed to give the desired compound as a colourless oil/gum, 105 mg, 90%. In order to remove the final traces of piperidine and free up the amine, the HCl salt was dissolved in DCM (3 ml) and to it added 3 ml of dry triethylamine. The solvent was then removed and the procedure repeated three more times to give the final product as a partial triethylamine salt.

m/z (LCMS ES+, 70V) 618.1 (MH+).

Intermediate 2

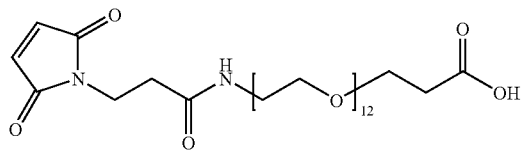

To Intermediate 1 (105 mg, 0.16 mmol) in DCM (6 ml) were added Et$_3$N (65 mg, 0.64 mmol) and maleimido propionic acid NHS ester (64 mg, 0.24 mmol). After 1 hour the solvent was removed, the residue dissolved in 0.1M HCl (25 ml), washed with Et$_2$O (4×25 ml) and extracted into DCM (10×30 ml). The combined DCM fractions were reduced to 30 ml, extracted into water (10×50 ml) and the water removed. The residue was dissolved in DCM, dried over MgSO$_4$ and the solvent removed to give the product 94 mg, 76% as a colourless oil/gum.

m/z (LCMS ES+, 70V) 769.0 (MH+).

$\delta_H$ (CDCl$_3$) 6.64 (2H, s), 6.59 (1H, br), 3.76 (2H, t, J7.1 Hz), 3.69 (2H, t, J6.3 Hz), 3.57 (44H, br), 3.47 (2H, t, J4.9 Hz), 3.34 (2H, br), 2.53 (2H, t, J6.3 Hz), 2.45 (2H, t, J7.1Hz).

Intermediate 3

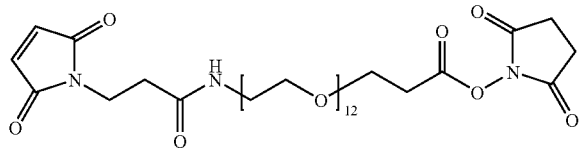

To Intermediate 2 (94 mg, 0.12 mmol) in DCM (8 ml) were added NHS (21 mg, 0.18 mmol) and EDC (35 mg, 0.18 mmol). After 4.5 hours the reaction was diluted to 50 ml with DCM and washed with 0.1M HCl (3×30 ml). The DCM was dried over MgSO$_4$ and the solvent removed to yield the NHS ester as a pale yellow, viscous oil 94 mg, 89%.

m/z (LCMS ES+, 70V) 866.1 (MH+).

$\delta_H$ (CDCl$_3$) 6.63 (2H, s), 6.58 (1H, br), 3.78 (4H, m), 3.57 (44H, m), 3.46 (2H, t, J5.0Hz), 3.34 (2H, br), 2.83 (2H, t, J6.4Hz), 2.75 (4H, s), 2.45 (2H, t, J7.2Hz).
Intermediate 4

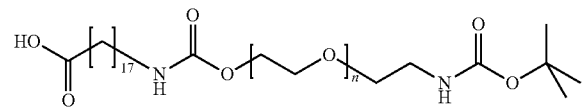

A suspension of Intermediate 23 (22 mg, 0.075 mmol) and Et$_3$N (25 mg, 0.25 mmol) in DMF (10 ml) was heated rapidly until a clear solution was obtained. To the solution was then added t-Boc-PEG-NHS, MW3400 (206 mg, 0.06 mmol) purchased from Shearwater and the solution allowed to cool. After 2 hours MP-Tosic acid resin (0.5 g, 1.43 mmol/g) was added and filtered off after 1 hour. The solvent was removed, the residue dissolved in 0.1M HCl (30 ml) and washed with Et$_2$O (4×40 ml). The aqueous solution was then extracted into DCM (4×40 ml), which was then washed with 0.1M HCl (3×30 ml), dried over MgSO$_4$ and the solvent removed to give the desired compound, 208 mg, 96% as a colourless waxy solid.

$\delta_H$(CDCl$_3$) 4.87 (1H, br), 4.22 (2H, t), 3.81 (2H, t, J4.9Hz), 3.64 (~336H, brs), 3.54 (2H, t, J5.2Hz), 3.46 (2H, t, J4.9Hz), 3.31 (2H, t, J5.1Hz), 3.15 (2H, t, J6.8Hz), 2.32 (2H, t, J7.5Hz), 1.63 (2H, t), 1.48 (2H, t), 1.44 (9H, s), 1.26 (26H, brs).
Intermediate 5

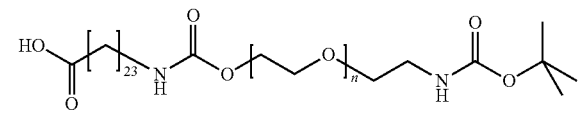

Method as for Intermediate 4, replacing Intermediate 23 with Intermediate 19. Yield 294 mg, 79%.
Intermediate 6

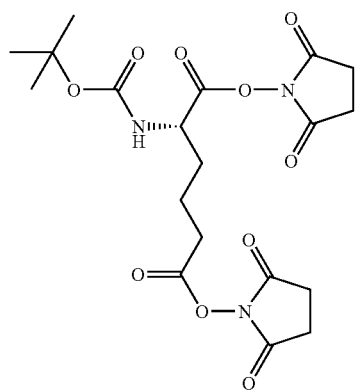

To a stirred solution/suspension of L-2-aminoadipic acid (460 mg, 2.85 mmol) in methanol (75 ml) was added Et$_3$N (866 mg, 8.56 mmol) followed by (BOC) 20 (934 mg, 4.28 mmol). The reaction was left overnight with a clear solution being obtained after approximately 45 min. The solvent was removed, the residue dissolved in DCM, and the solvent removed again. Addition and removal of DCM was repeated a further 5 times to ensure complete removal of the methanol. The residue was then dissolved in DCM (25 ml), to this added NHS (493 mg, 4.28 mmol) and EDC (821 mg, 4.28 mmol) and the reaction left overnight. The solution was washed with water (3×40 ml), dried over MgSO$_4$, and the solvent removed. The residue was purified by silica column chromatography eluting with 50-75% EtOAc in Hexane to yield the desired compound as a colourless solid 256 mg, 20%.

m/z (LCMS ES+, 70V) 478.1 (MNa+).

$\delta_H$ (CDCl$_3$) 4.97 (1H, br), 4.61 (1H, br), 2.74 (8H, s), 2.61 (2H, m), 2.01 (1H, m), 1.85 (3H, m), 1.37 (9H, s).
Intermediate 7

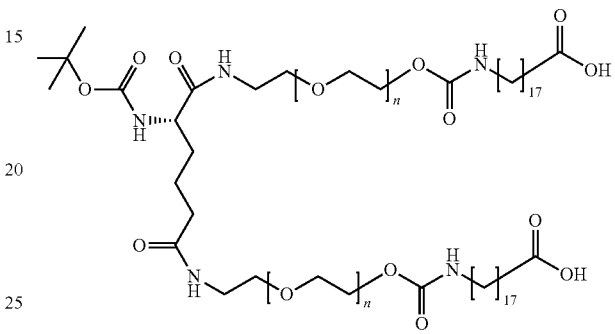

Intermediate 4 (0.045 mmol) was dissolved in 9:1 TFA:DCM (3 ml) and the solvent removed after 0.5 hours. The residue was dissolved in DCM (3 ml) and Et$_3$N (11 mg, 0.113 mmol) and Intermediate 6 (8.5 mg, 0.019 mmol) added and the reaction left for 3 days. The reaction was diluted to 20 ml with DCM and PS-TsCl resin (0.5 g, 1.45 mmol/g) added. After 1.5 hours the resin was filtered off, the filtrate washed with 0.1M HCl (3×30 ml), dried over MgSO$_4$ and the solvent removed to yield the desired material, 124 mg, 81%, as an off-white waxy solid.

m/z (LCMS ES−, 70V) for n=82, 2679 ((M-3H$^+$)$^{3-}$).

$\delta_H$ (CDCl$_3$) 6.88 (1H, t), 6.48 (1H, br), 5.30 (1H, m), 4.85 (2H, br), 4.20 (4H, m), 4.08 (1H, m), 3.75-3.30 (~650H, m), 3.08 (4H, m), 2.21 (4H, t), 2.18 (2H, m), 1.80-1.50 (8H, brm), 1.43 (4H, m), 1.37 (9H, s), 1.20 (52H, brs).
Intermediate 8

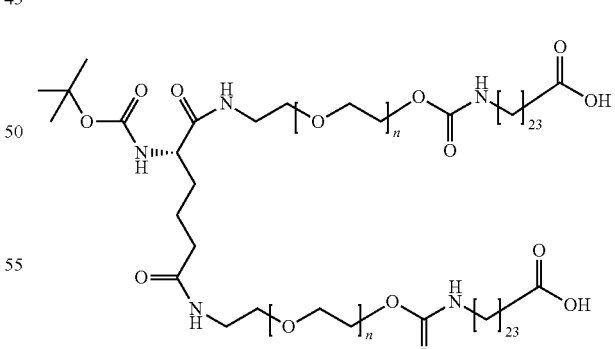

Method as for Intermediate 7 except Intermediate 5 is used in place of Intermediate 4.

$\delta_H$ (CDCl$_3$) 6.89 (1H, t), 6.47 (1H, t), 5.35 (1H, d, J7.9Hz), 4.90 (2H, br), 4.16 (4H, brm), 4.02 (1H, br), 3.80-3.30 (~650H, brm), 3.09 (4H, q, J6.8Hz), 2.24 (4H, t, J7.5Hz), 2.18 (2H, m), 1.80-1.50 (8H, brm), 1.43 (4H, m), 1.38 (9H, s), 1.20 (76H, br).

Intermediate 9

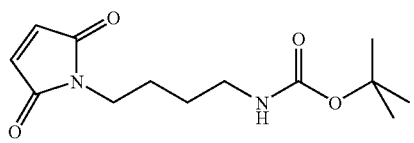

[4-(2,5-Dioxo-2,5-dihydro-pyrrol-1-yl)-butyl]-carbamic acid tert-butyl ester

Maleic anhydride (2.54 g, 26 mmol) and N-tBOC-1,4-diaminobutane (4.88 g, 26 mmol) were heated under reflux overnight using a Dean-Stark trap. The solvent was removed to yield a gum/oil. The oil fraction dissolved in DCM and was loaded onto a silica column and eluted with 2:1 hexane: EtOAc to afford the product, 1.85 g, 27% as a white solid.

m/z (ES+, 70V) 291.0 (MNa+), 169.0 (M-BOC.H+).

δ$_H$ (CDCl$_3$) 6.62 (2H, s), 4.45 (1H, br), 3.47 (2H, t, J7.1Hz), 3.06 (2H, q, J6.5Hz), 1.53 (4H, m), 1.37 (9H, s).

Intermediate 10

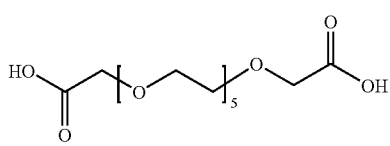

To a solution of NaH (60% in oil) (2.17 g, 0.054 mol) in THF (30 ml) and DCM (30 ml) at 0° C. was added over 15 min a solution of pentaethylene glycol (5.17 g, 0.022 mol) in THF (10 ml). The reaction was stirred for 1 hour at 0° C. and t-butyl bromoacetate (10.6 g, 0.054 mol) added rapidly (~10 sec.— CARE! effervescence). The reaction was maintained at 0° C. for a further 1 hour then allowed to warm to ambient temperature overnight. The reaction was filtered, the solvent was removed and the residue purified by silica column chromatography eluting with DCM followed by EtOAc to elute the di-$^t$butyl ester. To this material was added THF (20 ml) and water (20 ml) and to the rapidly stirred biphase/emulsion added LiOH (2 g). After 4 days the solution was acidified to pH1 and the solvent removed. The soluble residues were then taken up in DCM, dried over MgSO$_4$ and the solvent removed to yield the di-acid as a pale oil ~5 g.

m/z (LCMS ES+, 70V) 371.9 (MNH$_4$+).

Intermediate 11

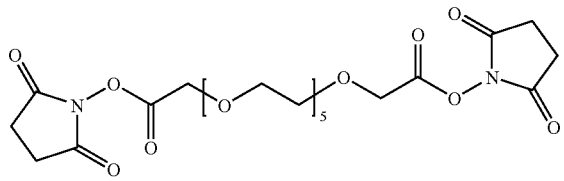

Intermediate 10 (~2 g) was dissolved in DMF (30 ml) and to it added EDC (4.9 g, ~3 equiv.) and NHS (2.9 g, ~3 equiv.). After overnight NHS ester formation the DMF was removed and the residue dissolved in DCM (100 ml). The DCM solution was washed with water (5×75 ml), dried over MgSO$_4$ and the solvent removed to yield impure di-NHS ester. The residue was purified by silica column chromatography eluting with EtOAc to yield the product as a colourless viscous oil/gum 970 mg.

m/z (LCMS ES+, 70V) 566.0 (MNH$_4$+).

δ$_H$ (CDCl$_3$) 4.55 (4H, s), 3.81 (4H, m), 3.74 (4H, m), 3.68 (12H, s), 2.87 (8H, s).

Intermediate 12

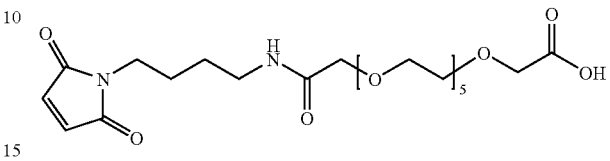

Intermediate 9 (98 mg, 0.36 mmol) was dissolved in 9:1 TFA:DCM (2 ml) and the solvent removed after 25 min. The residue was dissolved in DMF (1 ml) and added to a solution of Intermediate 11 (200 mg, 0.36 mmol) and Et$_3$N (184 mg, 1.8 mmol) in DCM (4 ml). NB May require more Et$_3$N to obtain a basic solution after TFA salt addition. After overnight reaction all the remaining NHS esters had hydrolysed to the acid. The solvent was removed, the residue dissolved in 0.1M HCl (30 ml) and extracted into DCM (3×30 ml), leaving the di-acid behind. The DCM solution containing the desired material and the di-maleimide was rapidly passed through 1" of silica eluting with 10% methanol in DCM to remove the di-maleimide, followed by MeOH to elute the product, 29 mg. NB The methanol must be removed within a few minutes to avoid it reacting with the maleimide-pink solution!

m/z (LCMS ES+, 70V) 505.0 (MH+).

δ$_H$ (CDCl$_3$) 7.06 (1H, brt), 6.63 (2H, s), 3.90 (2H, s), 3.86 (2H, brs), 3.58 (20H, br), 3.46 (2H, t, J7.0Hz), 3.22 (2H, q, J6.7Hz), 1.55 (2H, m), 1.46 (2H, m).

Intermediate 13

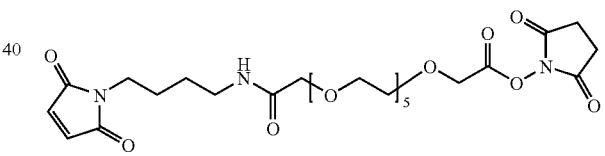

Intermediate 12 (29 mg, 0.058 mmol) was dissolved in DCM (4 ml) and to the solution added NHS (9.9 mg, 0.086 mmol) followed by EDC (16.5 mg, 0.086 mmol). The reaction was left at ambient temperature overnight, the reaction diluted to 40 ml with DCM and the solution washed with 0.1M HCl (4×30 ml). The DCM fraction was dried over MgSO$_4$ and the solvent removed to afford the NHS ester as a colourless gum (30 mg). This was used immediately in the preparation of Example 8.

m/z (LCMS ES+, 70V) 602.0 (N4H+)

Intermediate 14

12-Aminododecanol hydrochloride

NH$_2$(CH$_2$)$_{11}$CH$_2$OH.HCl

12-Aminododecanoic acid (21.52 g, 100 mmol) was suspended in 100 cm$^3$ THF and borane THF complex (500 mmol, 1M solution) added. The reaction was left overnight and carefully quenched with methanol before evaporation to small bulk. The residue was suspended in 1M HCl (500 ml) and heated at 40° C. for 1 hr and left overnight. The white solid was filtered off and washed with cold 1M HCl. The product was recrystallised from 1M HCl, filtered off & dried over $P_2O_5$ in vacuo. Yield 18.70 g (79%). Mp 120° C. softens, 169° C. liquid.

$C_{12}H_{28}NOCl\cdot\frac{1}{3}H_2O$ requires C: 59.70%, H: 11.86%, N: 5.80%. Found: C: 59.65%, H: 11.82%, N: 5.76%. m/z (ES+, 70V) 202.1 (MH+).

$\delta_H$ ($CD_3CO_2D$) 3.64 (2H, t), 3.06 (2H, t), 1.73 (2H, m), 1.57 (2H, m), 1.2-1.5 (16H, m).

Intermediate 15

12-(Dibenzylamino)dodecanol $Bn_2N(CH_2)_{11}CH_2OH$

Intermediate 14 (15 g, 63.2 mmol) was suspended in a mixture of dichloromethane (150 ml) & saturated sodium carbonate in water (150 ml). Benzyl bromide (189.6 mmol, 33.7 g, 23.5 ml) was added slowly. The suspension cleared and reaction was complete after 4 hr. Aqueous ammonia (0.880, 30 ml) was added & the reaction left overnight. The organic layer was dried (magnesium sulphate) & evaporated to dryness. The residues were dissolved with vigorous stirring in refluxing hexane. The flask was left at −20° C. when crystals slowly appear. The crystals (Mp 45° C.) were filtered off, (18.03 g, 75%).

$C_{26}H_{39}N_1O_1$ requires C: 81.84%, H: 10.30%, N: 3.67%. Found: C: 81.64%, H: 10.24%, N: 3.54%. $C_{26}H_{39}N_1O_1$ requires 381. m/z (ES+, 70V) 382 (MH+).

$\delta_H$ (CDCl$_3$) 7.1-7.6 (10H, m), 3.64 (2H, t), 3.56 (4H, s), 2.41 (2H, t), 1.1-1.8 (22H, m).

Intermediate 16

12-(Dibenzylamino)dodecanal $Bn_2N(CH_2)_{11}CHO$

To a solution of anhydrous dimethylsulphoxide (30 mmol, 2.13 ml) in dichloromethane (200 ml) at −78° C. was added carefully oxalyl chloride (2.6 ml, 30 mmol) in dichloromethane (60 ml). After 15 mins Intermediate 15 (10 g, 26 mmol) was added in dichloromethane (60 ml) and the reaction stirred for 20 mins at −78° C. Triethylamine (28 ml) was added dropwise to the cold reaction. A precipitate formed and after 15 mins the reaction was allowed to reach room temperature. Water (100 ml) was added to the reaction which was extracted with dichloromethane. The organic layers were washed with water, dried (magnesium sulphate) & evaporated to dryness. The residue was chromatographed (SiO$_2$, hexane –10% ethyl acetate in hexane) to give the product as an oil (7.97 g, 80%). This compound is unstable and should be used on the day of preparation.

I.R. 1725 cm$^{-1}$ (COH). $C_{26}H_{37}NO$ requires 379.29. m/z (ES+, 70V) 380.3 (MH+).

$\delta_H$ (CDCl$_3$) 1.32 (14H, br), 1.61 (4H: 2×p), 2.43 (2H, t), 2.44 (2H, t), 3.60 (4H, s), 7.2-7.5 (10H, m), 9.78 (1H, t). $\delta_C$ (CDCl$_3$) 22.0, 26.9, 27.1, 29.0, 29.3, 29.4, 29.5 (9C), 43.8 (1C), 53.3 (1C), 58.2 (2C), 126.6 (2C), 128.0 (4C), 128.6 (4C), 140.0 (2C), 202.3 (1C).

Intermediate 17

11-(Carboxyundecyl)triphenylphosphonium bromide $Ph_3P^+(CH_2)_{11}CO_2H.Br^-$

To 12-bromododecanoic acid (3.000 g, 10.7 mmol) suspended in acetonitrile (12 ml) was slowly added triphenylphosphine (2.818 g, 10.7 mmol). The reaction was heated at 100° C. (no condenser) with argon blowing over the flask until the reaction was a fusion, then maintained at 100° C. (with condenser) for 24 hrs. The warm residues were dissolved in acetonitrile (18 ml) and added dropwise to rapidly stirred cold (dry ice) diethyl ether. The white precipitate of phosphonium salt formed was then filtered off and the dried (5.353 g, 92%).

Mp 110-112° C. $C_{30}H_{38}O_2PBr$ requires C: 66.54%, H: 7.07%. Found: C: 66.42%, H: 7.10%.

$\delta_p$ (CDCl$_3$) 24.3 (s). $\delta_H$ (CDCl$_3$) 1.05-1.30 (12H, br), 1.53 (6H, br), 2.28 (2H, t), 3.55 (2H, br), 7.6-7.8 (15H, m). $\delta_C$ (CDCl$_3$) 22.1, 22.3, 22.8, 24.5, 28.8, 28.9, 30.0, 30.2 (10C), 34.2 (1C), 117.3, 118.7 (3C), 130.3, 130.5 (6C), 133.3, 133.5 (6C), 134.9 (3C), 177.4 (1C).

Intermediate 18

24-(Dibenzylamino)-12-tetracosenoic acid $Bn_2N(CH_2)_{11}CH{=}CH(CH_2)_{10}CO_2H$ Intermediate 17 (13.52 g, 25 mmol) was dissolved in dry DMSO (or THF) (40 ml) under argon at ~0° C. (no DMSO solidification). 2.2 equivalents of 2.0M LDA. (25 ml) was added, the solution turning orange. The reaction was left at 0° C. for ½ hour, and to the now dark orange solution was added a solution of Intermediate 16 (7.97 g, 21 mmol) in dry THF (30 ml). The solution was maintained at 0° C. for 4 hours then added to 2M HCl (50 ml). The aqueous layer was extracted with dichloromethane, the fractions combined, dried (MgSO$_4$) and the solvent removed to yield the crude material as a pale yellow gum. Silica column chromatography (30-100% ethyl acetate in hexane) yielded the desired product (6.20 g, 53%), as a pale yellow gum.

m/z (ES+, 70V) 562.5 (MH+), (ES−, 70V) 560.5 (M-H$^+$)$^-$.

$\delta_H$ (CDCl$_3$) 1.26 (30H, br), 1.42-1.72 (4H, m), 2.02 (4H, dxt), 2.34 (2H, t), 2.46 (2H, t), 3.65 (4H, s), 5.36 (2H, t), 7.2-7.4 (10H, m). $\delta_C$ (CDCl$_3$) 25.0, 26.4, 27.2, 29.3, 29.6 (19C), 34.5 (1C), 52.9 (1C), 57.7 (2C), 127.0 (2C), 128.2 (4C), 129.1 (4C), 129.9 (2C), 138.6 (2C), 179.2 (1C).

Intermediate 19

24-Aminotetracosanoic acid $NH_2(CH_2)_{23}CO_2H$

Intermediate 18 (6.2 g) under an atmosphere of hydrogen was heated at 60° C. overnight in glacial acetic acid using Pearlman's catalyst (10% w/w). The reaction was filtered through glass fiber & evaporated to dryness. The product was crystallised from acetic acid/ether (4.2 g, 100%). The product was subjected to high vacuum to remove traces of acetic acid.

Mp 151-155° C. $C_{24}H_{49}NO_2$. 0.75 $CH_3CO_2H$ requires C: 71.44%, H: 12.23%, N: 3.27%. Found: C: 71.43%, H: 12.15%, N: 3.26%. m/z (ES+, 70V) 384.3 (MH+).

$\delta^H$ (CD$_3$OD+TFA) 1.32 (38H, br), 1.65 (4H, br), 2.33 (2H, t), 2.74 (2H, m). $\delta_C$ (CD$_3$OD+TFA) partial 33.8 (1C), 35.3 (1C).

Intermediate 20

6-(Dibenzylamino)-1-hexanol $Bn_2N(CH_2)_5CH_2OH$

Benzyl bromide (61 ml, 511 mmol) was added to a stirred solution of 6-amino-1-hexanol (20 g, 170 mmol) and triethylamine (142 ml, 1.02 mol) in acetonitrile (500 ml) at room temperature for two days. The acetonitrile solution was concentrated to 100 ml and diluted with water. The aqueous phase was extracted with ethyl acetate, washed with brine, dried (magnesium sulphate) & evaporated to dryness to yield an orange oil. The product was chromatographed on silica (hexane—50% ethyl acetate/hexane) to yield a colourless oil (25 g, 50%).

$\delta^H$ (CDCl$_3$) 7.23-7.39 (10H, m), 3.59 (6H, m), 2.42 (2H, t), 1.47-1.56 (4H, m), 1.24-1.32 (4H, m).

Intermediate 21

6-(Dibenzylamino)hexanal

Bn$_2$N(CH$_2$)$_5$CHO

To a stirred solution of DMSO (20 mmol, 1.41 ml) in dichloromethane (100 ml) at −78° C. was carefully added oxalyl chloride (1.7 ml, 20 mmol) in dichloromethane (30 ml). After 15 mins Intermediate 20 (5 g, 16.83 mmol) was added in dichloromethane (30 ml) maintaining the temperature at −78° C. The reaction was stirred for 20 mins and triethylamine (14 ml) added dropwise. A precipitate formed, after 15 mins the reaction was allowed to reach room temperature. Water (100 ml) was added to the reaction which was extracted with dichloromethane. The organic layers were washed with water, dried (magnesium sulphate) & evaporated to dryness. The residue was chromatographed (SiO$_2$, hexane −20% ethyl acetate in hexane) to give the product as an oil (4.10 g, 83%). C$_{20}$H$_{25}$NO requires C: 81.31%, H: 8.53%, N: 4.74%. Found: C: 81.00%, H: 8.49%, N: 4.63%. m/z (ES+, 70V) 296 (MH+).

$\delta^H$ (CDCl$_3$) 9.71 (1H, s), 7.2-7.5 (10H, m), 3.57 (4H, s), 2.3-2.5 (4H, dt), 1.2-1.7 (6H, dm).

Intermediate 22

18-(Dibenzylamino)-12-octadecenoic acid

Bn$_2$N(CH$_2$)$_5$CH=CH(CH$_2$)$_{10}$CO$_2$H

Intermediate 17 (1.082 g, 2 mmol) was dissolved in dry DMSO (5 cm$^3$) under argon at ~0° C. (no DMSO solidification). 2.2 equivalents of 2.0M LDA (4 ml) was added, the solution turning orange. The reaction was left at 0° C. for ½ hour, and to the now dark orange solution was added a solution of Intermediate 21 (0.7 g, 2 mmol) in dry THF (10 ml). The solution was maintained at 0° C. for 4 hours then added to 2M HCl (50 ml). The aqueous layer was extracted with ethyl acetate, the fractions combined, dried (MgSO$_4$) and the solvent removed to yield the crude material as a pale yellow gum. Silica column chromatography (30% ethyl acetate in hexane or 5% methanol in dichloromethane) yielded the desired product (453 mg, 53%), as a low melting (Mp 21° C.) white solid.

C$_{32}$H$_{47}$NO$_2$ requires C: 80.45%, H: 9.92%, N: 2.93%. Found: C: 80.20%, H: 9.92%, N: 2.74%. C$_{38}$H$_{59}$NO$_2$ requires 477. Found m/z (ES+, 70V) 478 (MH+).

$\delta_H$ (CDCl$_3$) 8.6-9.2 (1H, vbr), 7.39-7.21 (10H, m), 5.37-5.29 (2H, m), 3.63 (4H, s), 2.48-2.43 (2H, t), 2.36-2.31 (2H, t), 2.01-1.97 (2H, t), 1.66-1.55 (4H, m), 1.29-1.24 (18H, m).

Intermediate 23

18-Aminooctadecanoic acid

NH$_2$(CH$_2$)$_{17}$CO$_2$H

Intermediate 22 (13 g) under an atmosphere of hydrogen was heated at 60° C. overnight in glacial acetic acid with Pearlman's catalyst (10% w/w). The reaction was filtered hot through glass fibre & evaporated to dryness. The product was crystallised from acetic acid/ether (8.2 g, 100%). The product was subjected to high vacuum to remove traces of acetic acid.

Mp 162-163° C. C$_{24}$H$_{49}$NO$_2$. 0.25H$_2$O requires C: 71.12%, H: 12.43%, N: 4.61%.

Found: C: 71.20%, H: 12.35%, N: 4.49%. m/z (ES+, 70V) 300 (MH+).

$\delta_H$ (CD$_3$CO$_2$D) 3.06 (2H, t), 2.38 (2H, t), 1.63-1.73 (4H, m), 1.33 (26H, m).

Intermediate 24

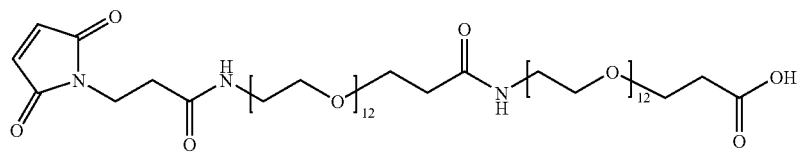

To a solution of Intermediate 3 (99 mg, 0.115 mmol) in DCM (3 ml) were added Et$_3$N (46 mg, 0.458 mmol) and Intermediate 1 (0.143 mmol). After 2 hours MP-Tosic acid (1 g, 1.43 mmol/g) was added, stirred for 1 hour and removed by filtration. The solvent was removed, the residue dissolved in 0.1M HCl (20 ml), washed with diethyl ether (5×30 ml) and extracted into DCM (10×20 ml). The DCM fractions were combined, washed with 0.1M HCl (20 ml), dried over MgSO$_4$ and the solvent removed to yield the product 120 mg, 77% as a pale yellow oil.

m/z (ES+, 70V) 685 (MH$_2^{2+}$).

$\delta_H$ (CDCl$_3$) 6.75 (1H, brt), 6.70 (2H, s), 6.33 (1H, brt), 3.76 (2H, t, J7.3Hz), 3.68 (4H, m), 3.57 (88H, m), 3.47 (4H, m), 3.34 (4H, m), 2.53 (2H, t, J6.4Hz), 2.45 (2H, t, J7.3Hz), 2.41 (2H, t, J6.0Hz).

Intermediate 25

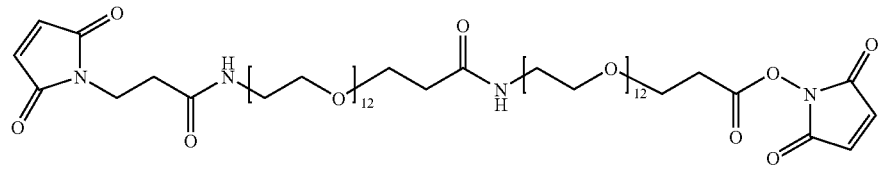

To a solution of Intermediate 24 (109 mg, 0.080 mmol) in DCM (4 ml) were added NHS (14 mg, 0.120 mmol) followed by EDC (23 mg, 0.120 mmol). After overnight reaction the solution was diluted with DCM to 40 ml, washed with 0.1M HCl (5×30 ml), dried over MgSO$_4$ and the solvent removed to give the product 103 mg, 88% as a colourless oil/gum.

m/z (ES+, 70V) 733 (MH$_2^{2+}$).

$\delta_H$(CDCl$_3$) 6.63 (2H, s), 6.62 (1H, brt), 6.37 (1H, brt), 3.78 (4H, m), 3.67 (2H, t, J6.0Hz), 3.56 (88H, br), 3.46 (4H, m), 3.35 (4H, m), 2.83 (2H, t, J6.5Hz), 2.77 (4H, s), 2.44 (2H, t, J7.2Hz), 2.40 (2H, t, J6.0Hz).

Intermediate 26

9-Phthalimidononan-1-ol

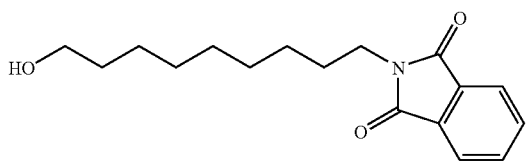

A stirred mixture of 9-bromononanol (Aldrich)(1.0 g, 4.5 mmol), phthalimide potassium derivative (1.85 g, 10 mmol) and DMF (10 ml) was heated at 100° C. for 1 hour. The mixture was allowed to cool to room temperature and was partitioned between ethyl acetate and water. The organic layer was washed with water, brine, dried over magnesium sulfate and evaporated under reduced pressure to afford the title compound as a white solid, 1.53 g, quantitative yield. m/z (LCMS ES+, 70 v) 290.1 (MH$^+$), 312.1 (MNa$^+$). $\delta$H (CHCl$_3$-d) 7.81 (2H, m), 7.73 (2H, m), 3.64 (4H, m), 1.68 (2H, m), 1.59 (2H, m), 1.32 (10H, m).

Intermediate 27

9-Phthalimidononan-1-al

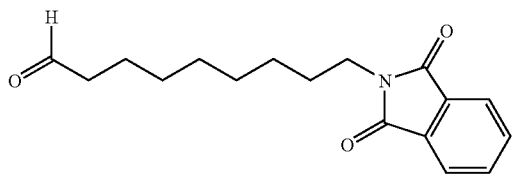

To a stirred solution of dimethylsulfoxide (0.568 ml, 8.0 mmol) in dichloromethane (50 ml) at −78° was added oxalyl chloride (0.693 ml, 8.0 mmol) dropwise. The mixture was stirred at −78° for 15 minutes. Intermediate 26 (2.0 g, 7.0 mmol) in dichloromethane (8 ml) was added slowly. The mixture was stirred at −78° for 20 minutes. Triethylamine (7.5 ml) was added. The mixture was stirred at −78° for 15 minutes and allowed to warm to room temperature. Water was added; the layers were separated and the organic layer was washed with water, brine, dried over magnesium sulfate and evaporated under reduced pressure to afford the title compound as an oil, 2.18 g, quantitative yield. The product had a higher Rf than the starting material by TLC (1:1 hexane:ethyl acetate; visualised with UV light). $\delta$H(CHCl$_3$-d) 9.68 (1H, s), 7.77 (2H, m), 7.64 (2H, m), 3.60 (t, 2H, J=7.5Hz), 2.33 (t, 2H, J=7.4Hz), 1.54 (4H, m), 1.25 (8H, m).

Intermediate 28

(8-Carboxyethyl)octyl bromide

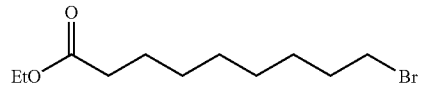

To stirred ethanol (100 ml) was added acetyl chloride (10 ml) slowly. The solution was stirred for 30 minutes. 9-Bromononan-1-oic acid (3.50 g, 14.8 mmol) (prepared according to the method of. Tranchepain et al, Tetrahedron volume 45, page 2060 (1989)) was added and the resulting solution heated at reflux for 1 hour. The reaction was observed to be complete by TLC (1:1 hexane:ethyl acetate; visualised with ceric sulphate); the product had a higher Rf than the starting material. The solvent was evaporated under reduced pressure to afford the title compound (along with a side product thought to be the chloro analog of the title compound) as a yellow oil, 3.52 g. $\delta_H$ (CHCl$_3$-d) 4.15 (2H, q, J=7.2Hz), 3.42 (2H, t, J=6.8Hz), 2.31 (2H, t, J=7.5Hz), 1.87 (2H, m), 1.62 (2H, m), 1.45 (2H, m), 1.34 (8H, m), 1.27 (3H, t, J=7.2Hz).

Intermediate 29

(8-Carboxyethyl)octyltriphenylphosphonium bromide

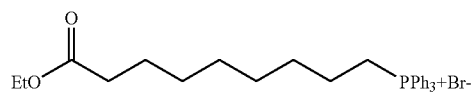

A mixture of the crude Intermediate 28 (3.50 g, 14.8 mmol) and triphenylphosphine (3.88 g, 14.8 mmol) was heated at 110° for 72 hours. Disappearance of starting material was confirmed by TLC (1:1 hexane:ethyl acetate; visualised with ceric sulphate). The reaction mixture was allowed to cool to room temperature and triturated with isopropyl ether to afford the title compound as a yellow oil, 2.25 g, 29%. $\delta$H(DMSO-d6) 7.90-7.73 (15H, m), 4.04 (2H, q, J=7.1Hz), 3.60 (2H, m), 2.24 (2H, t, J=7.3Hz), 1.50 (4H, m), 1.24 (8H, m), 1.16 (3H, t, J=7.1Hz).

Intermediate 30

Z-18-Phthalimidoethyl-9-octadecanoate

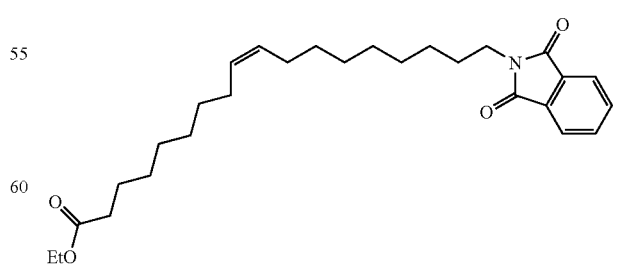

To a stirred solution of Intermediate 29 (2.25 g, 4.3 mmol) in anhydrous tetrahydrofuran (20 ml) at −78° was added a solution of potassium bis(trimethylsilyl)amide 0.5M in toluene (8.6 ml, 4.3 mmol) dropwise over 5 minutes. The solution was allowed to warm to 0°, re-cooled to −78° and a solution of Intermediate 27 (1.20 g, 4.1 mmol) in anhydrous tetrahydrofuran (9 ml) was added dropwise over 5 minutes. The mixture was stirred for 30 minutes at −78°, allowed to warm to room temperature and stirred for a further 30 minutes before quenching with water (40 ml). The organic layer was separated, washed with brine, dried over magnesium sulfate and evaporated under reduced pressure to afford 2.0 g yellow oil. Chromatography on silica gel; mobile phase 10:1 hexane: ethyl acetate loading in toluene gave the title compound as a yellow oil, 380 mg, (20%). $\delta_H$ ($C_6H_6$-d6) 7.59 (2H, dd, J=3.0, 5.4Hz), 7.00 (2H, dd, J=3.0, 5.4Hz), 5.58 (2H, m), 4.10 (2H, q, J=7.1Hz), 3.65 (2H, t, J=7.3Hz), 2.26 (2H, t, J=7.4Hz), 2.20 (2H, m), 1.70 (2H, m), 1.44 (2H, m), 1.30 (20H, m), 1.10 (3H, t, J=7.1Hz).

Intermediate 31

Z-18-Amino-9-octadecenoic acid

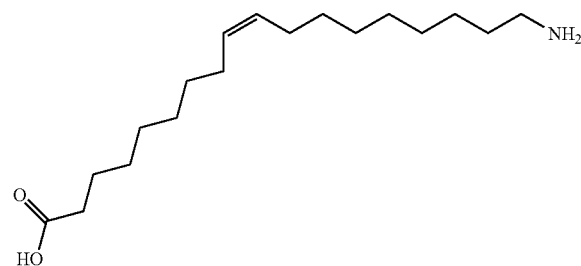

Intermediate 30 (100 mg, 0.22 mmol), ethanol (2 ml), water (2 ml) and sodium hydroxide (1.0 g) were heated together at reflux for 48 hours. The reaction was found to have proceeded to completion by TLC (200:20:3:2 dichloromethane:methanol:acetic acid:water; visualizing with ninhydrin). The reaction mixture was allowed to cool to room temperature, acidified with 2M hydrochloric acid and extracted with ethyl acetate. The extract was washed with brine and loaded onto the top of a silica gel column.

Chromatography; mobile phase dichloromethane:methanol:acetic acid:water 400:20:3:2 followed by 200:20:3:2 gave the title compound as a white solid, 38 mg, (58%). m/z (LCMS ES+, 70 v) 298.0 MH$^+$

EXAMPLE 1

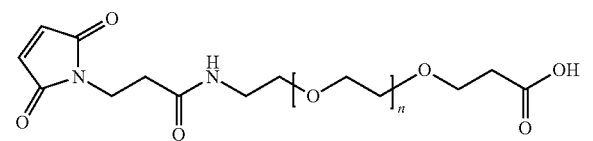

NHS-PEG-MAL, MW 2000 (50 mg) purchased from Shearwater was dissolved in distilled water (2 ml) and left overnight. The solution was diluted with 0.1M HCl (20 ml) and extracted with DCM (4×25 ml). The combined DCM fractions were then washed with 0.1M HCl (2×20 ml), dried over MgSO$_4$ and the solvent removed to give the acid as a waxy white solid, 43 mg, 90%.

m/z (LCMS ES−, 60V) for n=43 2177 ((M-H$^+$)$^-$).

$\delta_H$ (CDCl$_3$) 6.64 (2H, s), 6.37 (1H, br), 3.80-3.64 (4H: 2×m). 3.6-3.3 (~176H, brm), 2.53 (2H, J6.3Hz) 2.45 (2H, t, J7.2Hz).

EXAMPLE 2

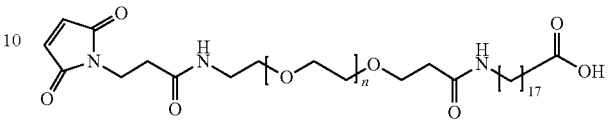

A suspension of Intermediate 23 (12 mg, 0.04 mmol) and Et$_3$N (13 mg, 0.133 mmol) in DMF (5 ml) was rapidly heated until a clear solution was obtained. To the solution was then added NHS-PEG-MAL, MW 3400 (113 mg, 0.033 mmol) from Shearwater and the reaction left with no heating for 1 hour. MP-Tosic acid resin (0.5 g, 1.43 mmol/g) was added, stirred for 2 hours, filtered off and the solvent removed from the filtrate. The resulting residue was dissolved in 0.1MHCl (20 ml), washed with Et$_2$O (5×50 ml), extracted into DCM (4×30 ml) and the combined DCM fractions washed with 0.1M HCl (3×30 ml). The DCM was dried over MgSO$_4$ and the solvent removed to yield the product as an off white waxy solid 108 mg, 91%.

m/z (LCMS ES−, 60V) for n=73 1890 ((M-2H$^+$)$^{2-}$).

$\delta_H$ (CDCl$_3$) 6.70 (2H, s), 3.88-3.59 (4H, s), 3.66-3.50 (~290H, br), 3.54 (2H, m), 3.46 (2H, m), 3.42 (2H, t, J4.9Hz), 3.30 (2H, t, J7.1Hz), 2.79 (2H, t), 2.53 (2H, t, J7.2Hz), 2.32 (2H, t, J7.5), 1.63 (2H, m), 1.55 (2H, m), 1.26 (26H, br).

EXAMPLE 3

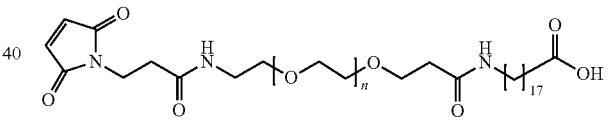

Method as for Example 2 except replaced NHS-PEG-MAL, MW 3400 with NHS-PEG-MAL, MW 2000.

m/z (LCMS ES−, 60V) for n=44 2458 ((M-H$^+$)$^-$).

$\delta_H$ (CDCl$_3$) 6.70 (2H, s), 6.53 (2H, br), 3.80-3.42 (~160H, brm), 3.39 (2H, t, J4.9Hz), 3.35 (2H, q, J5.1Hz), 3.15 (2H, q, J6.7Hz), 2.45 (2H, t, J7.2Hz), 2.40 (2H, t, J5.8Hz), 2.24 (2H, t, J5Hz), 1.54 (2H, m), 1.42 (2H, m), 1.18 (26H, br).

EXAMPLE 4

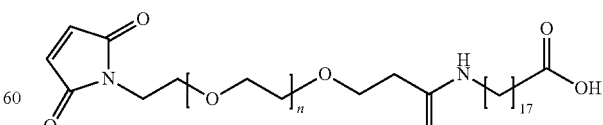

Method as for Example 2 except replaced NHS-PEG-MAL, MW 3400 with Nektar's new NHS-PEG-MAL, MW 3400 and used DMSO in place of DMF.

m/z (ES) for n=78 1982 ((M-H$^+$Cl$^-$)$^{2-}$).

δ$_H$ (CDCl$_3$) 6.64 (2H, s), 6.46 (1H, bit), 3.88-3.46 (316H, brm), 3.40 (2H, t, J4.9Hz), 3.15 (2H, q, J6.7Hz), 2.40 (2H, t, J5.7Hz), 2.24 (2H, t, J7.5H), 1.56 (2H, p), 1.42 (2H, p), 1.18 (26H, br).

EXAMPLE 5

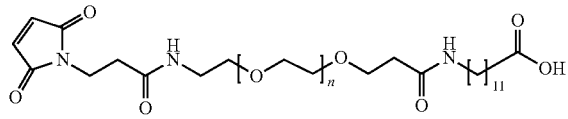

Method as for Example 2 except replaced Intermediate 23 with 12-amino dodecanoic acid.

m/z (LCMS ES−, 60V) for n=74 1848 ((M-2H$^+$)$^{2-}$).

δ$_H$ (CDCl$_3$) 6.70 (2H, s), 3.90-3.69 (4H, m), 3.66-3.58 (~290H, m), 3.54 (2H, m), 3.46 (2H, m), 3.42 (2H, t, J4.9Hz), 3.31 (2H, t, J6.7Hz), 2.83 (2H, br), 2.54 (2H, t, J7.2Hz), 2.34 (2H, m), 1.63 (2H, m), 1.56 (2H, m), 1.28 (14H, br).

EXAMPLE 6

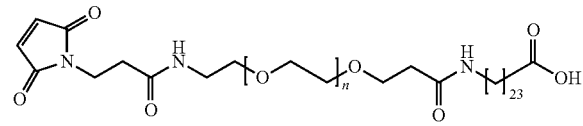

Method as for Example 2 except replaced Intermediate 23 with Intermediate 19 and replaced NHS-PEG-MAL, MW 3400 with NHS-PEG-MAL, MW 2000.

m/z (LCMS ES−, 60V) for n=43 2542 ((M-H$^+$)$^-$).

δ$_H$ (CDCl$_3$) 6.64 (2H, s), 6.54 (1H, br), 6.41 (1H, br), 3.80-3.45 (~160H, br), 3.39 (2H, t, J4.9Hz), 3.35 (2H, q, J5.1Hz), 3.15 (2H, q, J6.7Hz), 2.45 (2H, t, J7.3Hz), 2.41 (2H, t), 2.24 (2H, t, J7.5Hz), 1.55 (2H, p, J7.3Hz), 1.42 (2H, m), 1.19 (38H, s).

EXAMPLE 7

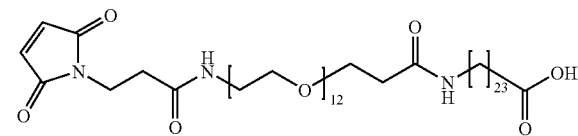

Method as for Example 2 except replaced Intermediate 23 with Intermediate 19 and replaced NHS-PEG-MAL, MW 3400 with Intermediate 3 and DMSO used in place of DMF.

m/z (LCMS ES+) 567.7 ((MH$_2$)$^{2+}$).

δ$_H$ (CDCl$_3$) 6.64 (2H, s), 6.68 (1H, brt), 6.63 (2H, s), 6.48 (1H, br), 3.77 (2H, t, J7.2Hz), 3.66 (2H, t, J5.7Hz), 3.57 (44H, brs), 3.47 (2H, t, J5.0Hz), 3.35 (2H, q, J4.9Hz), 3.16 (2H, q, J6.6Hz), 2.44 (4H, m), 2.25 (2H, t, J7.5Hz), 1.55 (2H, p, J7.4Hz), 1.42 (2H, P, J6.9Hz), 1.18 (38H, brs).

EXAMPLE 8

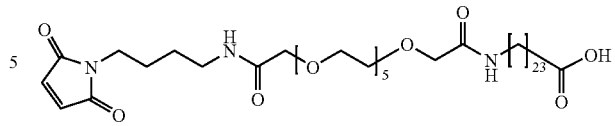

Method as for Example 2 except replaced Intermediate 23 with Intermediate 19 and replaced NHS-PEG-MAL, MW 3400 with Intermediate 13 and DMSO used in place of DMF.

m/z (LCMS ES+) 870.3 (MH+).

δ$_H$ (CDCl$_3$) 7.05 (1H, br), 6.98 (1H, br), 6.62 (2H, s), 3.94 (2H, s), 3.92 (2H, s), 3.59 (20H, br), 3.47 (2H, t, J7.0Hz), 3.23 (4H, m), 2.25 (2H, t, J7.5Hz), 1.56 (4H, m), 1.45 (4H, m), 1.18 (38H, brs).

EXAMPLE 9

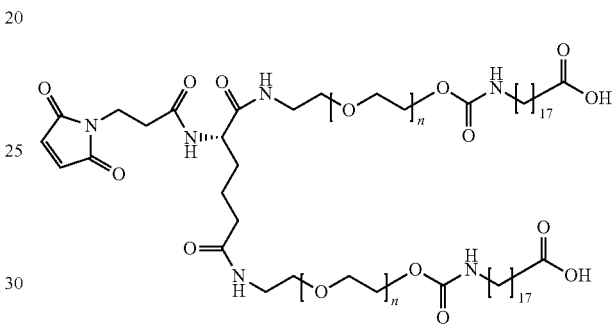

Intermediate 7 (124 mg, 0.015 mmol) was dissolved in 9:1 TFA:DCM (3 ml) and the solvent removed after 25 minutes. The residue was dissolved in DCM (3 ml), to this added Et$_3$N (9 mg, 0.088 mmol) (may need to add more to obtain a basic solution due to excess TFA) and maleimido propionic acid NHS ester (12 mg, 0.044 mmol). After overnight reaction the solvent was removed, the residue, the residue dissolved in 0.1M HCl (25 ml) and washed with Et$_2$O (10×40 ml). The aqueous layer was then extracted into DCM (3×30 ml), the combined DCM fractions washed with 0.1M HCl (3×30 ml) and the solvent removed to yield the title compound as an off white solid 80 mg, 64%.

δ$_H$ (CDCl$_3$) 7.01 (1H, brt), 6.90 (1H, d, J6.9Hz), 6.64 (2H, s), 6.52 (1H, t), 4.85 (2H, brt), 4.27 (1H, m), 4.14 (4H, m), 3.78-3.42 (~640H, brm), 3.39 (2H, m), 3.36 (2H, m), 3.08 (4H, m), 2.48 (2H, t, J7.0Hz), 2.23 (4H, m), 2.19 (2H, m), 1.73 (1H, m), 1.69-1.54 (7H, m), 1.41 (4H, m), 1.18 (52H, br).

EXAMPLE 10

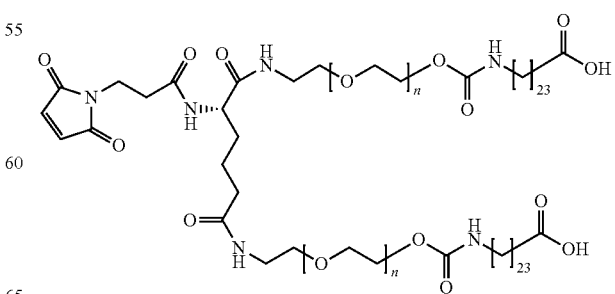

Method as for Example 9 except Intermediate 8 was used in place of Intermediate 7. 189 mg, 75%.

m/Z (ES−) 2751 n=80 ((M-3H$^+$)$^{3-}$).

$\delta_H$ (CDCl$_3$) 7.20 (1H, brs), 6.95 (1H, br), 6.85 (1H, br), 6.67 (2H, s), 4.84 (2H, br), 4.30 (1H, m), 4.18 (4H, m), 3.85-3.45 (~640H, br), 3.42 (4H, m), 3.10 (4H, m), 2.50 (2H, t), 2.27 (6H, m), 1.75 (1H, m), 1.7-1.5 (7H, m), 1.42 (4H, m), 1.20 (76H, br).

EXAMPLE 11

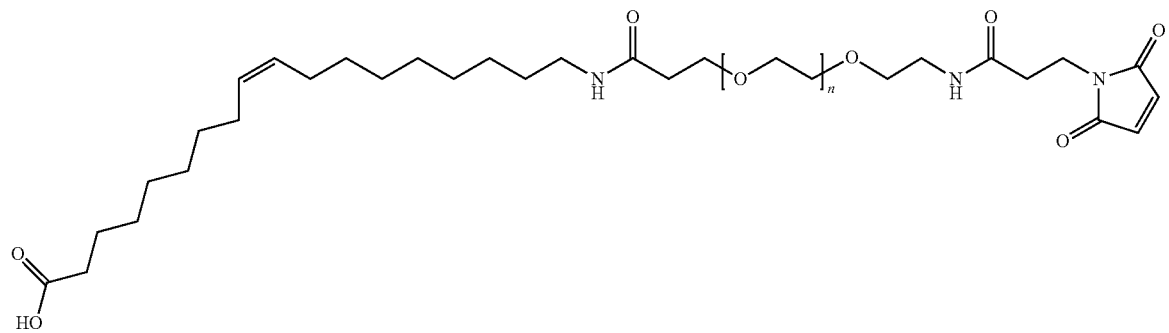

To a solution of Intermediate 25 (70 mg, 0.48 mmol) in DMSO (1.5 ml) was added a hot solution of Intermediate 19 (25 mg, 0.057 mmol) and Et$_3$N (24 mg, 0.239 mmol) in DMSO (2.5 ml) (heated with hot air gun until dissolved and immediately used). The reaction was allowed to cool to ambient temperature and after 4 hours MP-Tosic acid resin (200 mg, 1.43 mmol/g) added. After 1 hour the resin was filtered off, the solvent removed and the residue dissolved in DCM (40 ml). The DCM solution was washed with 0.1M HCl (5×25 ml), dried over MgSO4 and the solvent removed. The residue was then triturated with 0.1M HCl and the solvent removed to give the desired material 55 mg, 66% as a yellow solid.

m/z (ES+, 70V) 868 ((MH$_2$)$^{2+}$).

$\delta_H$ (CDCl$_3$) 6.68 (1H, br), 6.63 (2H, s), 6.50 (1H, br), 4.00-3.20 (102H, brm), 3.15 (2H, q, J6.7Hz), 2.41 (6H, br), 2.24 (2H, t, J7.4Hz), 1.55 (2H, p, J7.1Hz), 1.42 (2H, p, J6.9Hz), 1.18 (38H, br).

EXAMPLE 12

Method as for Example 2 except replaced Intermediate 23 with Intermediate 31 and the DMF with DMSO to afford the title compound as a waxy solid.

(LCMS ES+, 70 v) 1882.5 ((MNa$_2$)$^{2+}$).

$\delta_H$ (CDCl$_3$) 6.64 (1H, brs), 6.63 (2H, s), 6.38 (1H, brs), 5.27 (1H, m), 5.27 (1H, m), 3.77 (3H, m), 3.57 (~320H, m), 3.46 (2H, m), 3.35 (2H, m), 3.16 (2H, m), 2.44 (4H, m), 2.24 (2H, t, J=7.4Hz), 1.94 (4H, m), 1.55 (2H, m), 1.42 (2H, m), 1.22 (18H, m).

The invention claimed is:

1. An albumin-binding compound comprising a spacer group, a water-soluble bridging group, a fatty acid chain and an acidic group wherein the water-soluble bridging group is disposed between the spacer group and the fatty acid chain, the fatty acid chain is disposed between the water-soluble group and the acidic group, and the acidic group is attached to the distal end of the compound.

2. An albumin-binding compound according to claim 1 to which one or more biologically active moieties are attached.

3. An albumin-binding compound according to claim 2 selected from a compound of formula (I), (II), (III) and (IV):

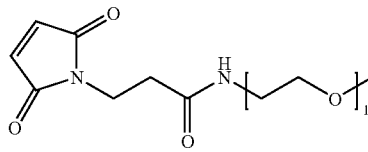

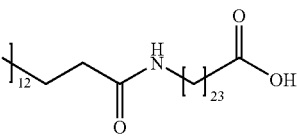

-continued

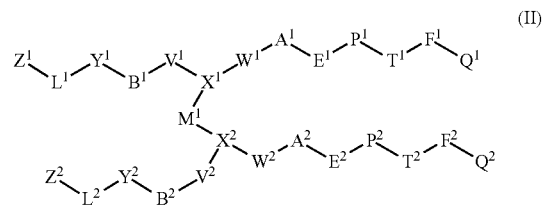

-continued

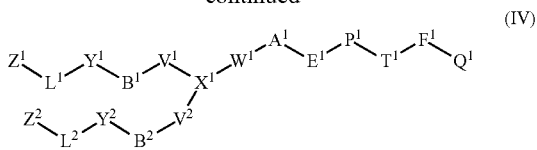
(IV)

wherein:
- Z, $Z^1$ and $Z^2$ each independently represent the residue of a biologically active moiety;
- L, $L^1$ and $L^2$ each independently represent a spacer group;
- Y, $Y^1$ and $Y^2$ each independently represent a covalent bond or —$(CH_2)_y$—;
- B, $B^1$ and $B^2$ each independently represent a covalent bond, —CONH—, —NHCO—, —CO—, —OC(O)N($R^2$)—, —N($R^2$)C(O)O— or —NHCONH—;
- $V^1$ and $V^2$ each independently represent a covalent bond or —$(CH_2)_v$—;
- $X^1$ and $X^2$ each independently represent $CR^1$ or N;
- $M^1$ represents a covalent bond or —$(CH_2)_m$—;
- $W^1$ and $W^2$ each independently represent a covalent bond or —$(CH_2)_w$—;
- $A^1$ and $A^2$ each independently represent —CONH—, —NHCO—, —CO—, —OC(O)N($R^2$)—, —N($R^2$)C(O)O— or —NHCONH—;
- E, $E^1$ and $E^2$ each independently represent a covalent bond or —$(CH_2)_e$—;
- P, $P^1$ and $P^2$ each independently represent a water-soluble bridging group;
- T, $T^1$ and $T^2$ each independently represent a covalent bond or a linker group;
- F, $F^1$ and $F^2$ each independently represent a fatty acid chain;
- Q, $Q^1$ and $Q^2$ each independently represent an acidic group;
- $R^1$ represents hydrogen or $C_{1-4}$ alkyl;
- $R^2$ represents hydrogen or $C_{1-4}$ alkyl;
- e is 1, 2, 3 or 4;
- v is 1, 2, 3 or 4;
- w is 1, 2, 3 or 4;
- y is 1, 2, 3, 4, 5 or 6; and
- m is 1, 2 or 3.

4. An albumin-binding compound according to claim 3 in which F, $F^1$ and $F^2$ are each independently a straight chain of between 11 and 24 carbon atoms.

5. An albumin-binding compound according to claim 4 in which F, $F^1$ and $F^2$ are each independently a straight chain of 17 or 23 carbon atoms.

6. An albumin-binding compound according to claim 3 in which Z, $Z^1$ and $Z^2$ are each the residue of an antibody or antibody fragment.

7. An albumin-binding compound according to claim 3 in which L, $L^1$ and $L^2$ are each succinimide.

8. An albumin-binding compound according to claim 3 in which P, $P^1$ and $P^2$ are each polymer moieties comprising the repeating unit [$OCH_2CH_2$], where n is between 5 and 100.

9. An albumin-binding compound according to claim 3 in which T, $T^1$ and $T^2$ are each independently selected from a covalent bond, —CONH—, $OCH_2CONH$—, —OCONH—, and —NHCO—.

10. An albumin-binding compound according to claim 3 in which Q, $Q^1$ and $Q^2$ are each $CO_2H$.

11. A compound of formula (V), (VI), (VII) or (VIII):

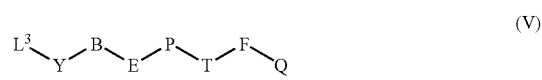
(V)

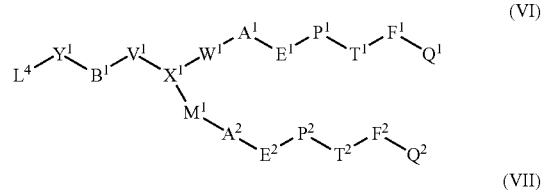
(VI)

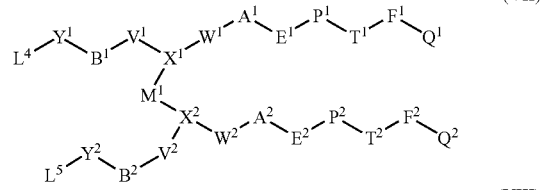
(VII)

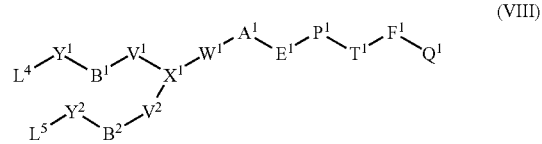
(VIII)

wherein $L^3$, $L^4$ and $L^5$ each independently represent groups capable of attaching the residue Z, $Z^1$ and $Z^2$ respectively, or capable of being converted into such groups;
- Z, $Z^1$ and $Z^2$ each independently represent the residue of a biologically active moiety;
- Y, $Y^1$ and $Y^2$ each independently represent a covalent bond or —$(CH_2)_y$—;
- B, $B^1$ and $B^2$ each independently represent a covalent bond, —CONH—, —NHCO—, —CO—, —OC(O)N($R^2$)—, —N($R^2$)C(O)O— or —NHCONH—;
- $V^1$ and $V^2$ each independently represent a covalent bond or —$(CH_2)_y$—;
- $X^1$ and $X^2$ each independently represent $CR^1$ or N;
- $M^1$ represents a covalent bond or —$(CH_2)_m$—;
- $W^1$ and $W^2$ each independently represent a covalent bond or —$(CH_2)_w$—;
- $A^1$ and $A^2$ each independently represent —CONH—, —NHCO—, —CO—, —OC(O)N(R)—, —N($R^2$)C(O)O— or —NHCONH—;
- E, $E^1$ and $E^2$ each independently represent a covalent bond or —$(CH_2)_e$—;
- P, $P^1$ and $P^2$ each independently represent a water-soluble bridging group;
- T, $T^1$ and $T^2$ each independently represent a covalent bond or a linker group;
- F, $F^1$ and $F^2$ each independently represent a fatty acid chain;
- Q, $Q^1$ and $Q^2$ each independently represent an acidic group;
- $R^1$ represents hydrogen or $C_{1-4}$ alkyl $R^2$ represents hydrogen or $C_{1-4}$ alkyl e is 1, 2, 3 or 4:
- v is 1, 2, 3 or 4;

w is 1, 2, 3 or 4, y is 1, 2, 3, 4, 5 or 6; and
m is 1, 2 or 3.

12. A compound according to claim 11 in which $L^3$, $L^4$ and $L^5$ are each maleimide derivatives.

13. A compound according to claim 12 selected from a compound of formula (IX), (X), (XI), and (XII):

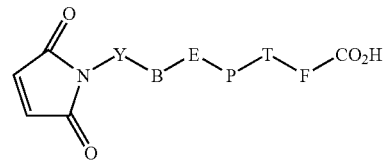
(IX)

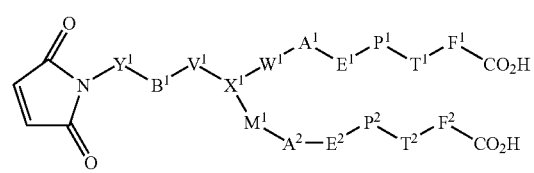
(X)

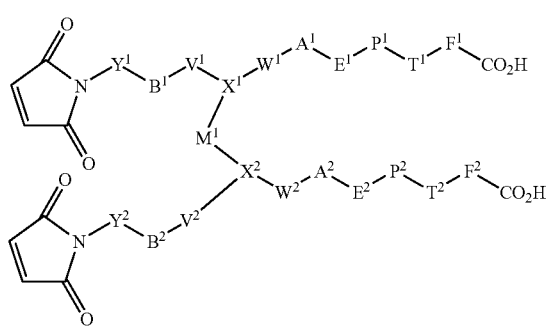
(XI)

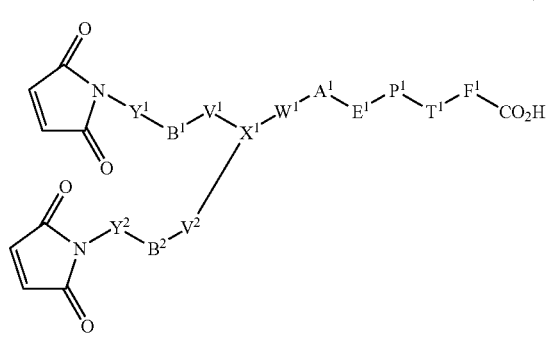
(XII)

wherein

Y, $Y^1$ and $Y^2$ each independently represent a covalent bond or —$(CH_2)_y$—;

B, $B^1$ and $B^2$ each independently represent a covalent bond, —CONH—, —NHCO—, —CO—, —OC(O)N($R^2$)—, —N($R^2$)C(O)O— or —NHCONH—;

$V^1$ and $V^2$ each independently represent a covalent-bond or —$(CH_2)_v$—;

$X^1$ and $X^2$ each independently represent $CR^1$ or N;

$M^1$ represents a covalent bond or —$(CH_2)_m$—;

W.sup.1 and W.sup.2 each independently represent a covalent bond or —$(CH_2)_w$—;

$A^1$ and $A^2$ each independently represent —CONH—, —NHCO—, —CO—, —OC(O)N($R^2$)—, —N($R^2$)C(O)O— or —NHCONH—;

E, $E^1$ and E2 each independently represent a covalent bond or —$(CH_2)_y$—;

P, $P^1$ and $P^2$ each independently represent a water-soluble bridging group;

T, $T^1$ and $T^2$ each independently represent a covalent bond or a linker group;

F, $F^1$ and $F^2$ each independently represent a fatty acid chain;

$R^1$ represents hydrogen or $C_{1-4}$ alkyl;

$R^2$ represents hydrogen or $C_{1-4}$ alkyl;

e is 1, 2, 3 or 4;

v is 1, 2, 3 or 4;

w is 1, 2, 3 or 4;

y is 1, 2, 3, 4, 5 or 6; and mis 1,2 or 3.

14. A compound according to claim 13 selected from

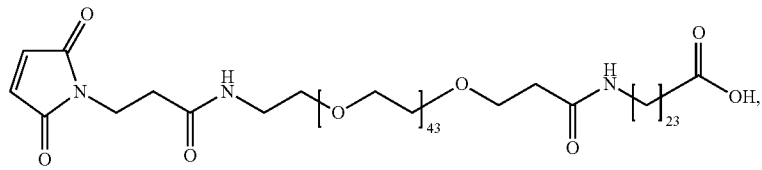

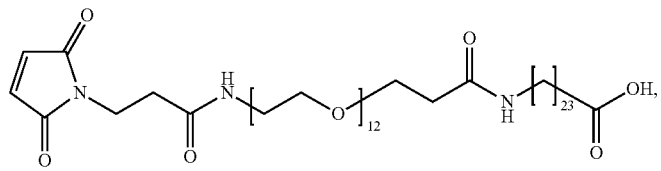

-continued
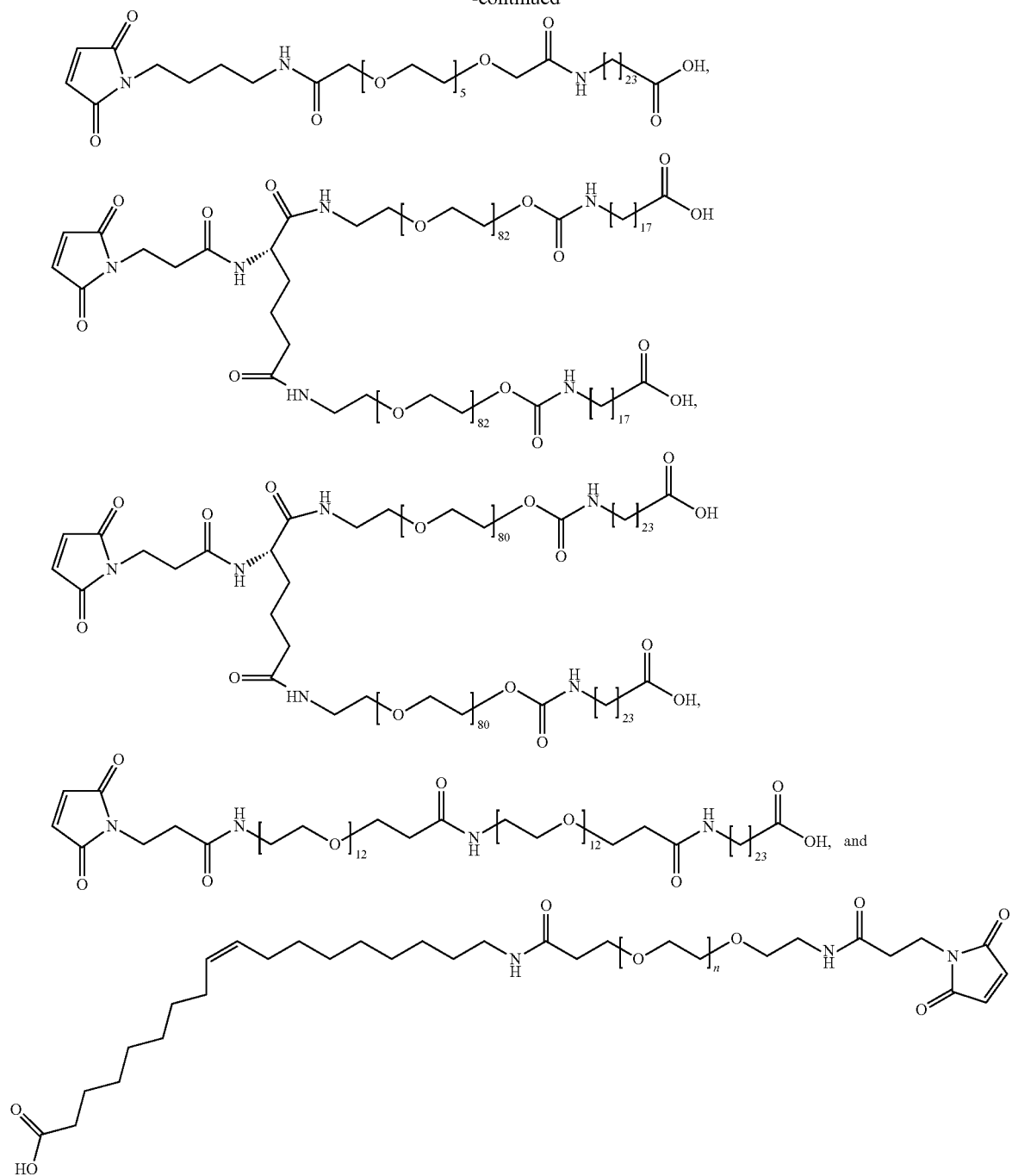
where n is between 5 and 100.
15. A pharmaceutical composition comprising a compound according to claim 2 in association with one or more pharmaceutically acceptable carriers, excipients or diluents.
* * * * *